(12) United States Patent
Tabib-Azar

(10) Patent No.: US 11,009,482 B1
(45) Date of Patent: May 18, 2021

(54) WHOLE VIRUS QUANTUM MECHANICAL TUNNELING CURRENT AND ELECTRONIC SENSORS

(71) Applicant: University of Utah Research Foundation, Salt Lake City, UT (US)

(72) Inventor: Massood Tabib-Azar, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 17/080,517

(22) Filed: Oct. 26, 2020

Related U.S. Application Data

(60) Provisional application No. 62/926,376, filed on Oct. 25, 2019, provisional application No. 63/021,605, filed on May 7, 2020.

(51) Int. Cl.
*G01N 27/414* (2006.01)
*G01N 33/543* (2006.01)
*G01N 33/569* (2006.01)

(52) U.S. Cl.
CPC ..... *G01N 27/4145* (2013.01); *G01N 33/5438* (2013.01); *G01N 33/56983* (2013.01); *G01N 2333/165* (2013.01); *G01N 2333/185* (2013.01)

(58) Field of Classification Search
CPC .......... G01N 27/4145; G01N 33/5438; G01N 33/56983; G01N 2333/165; G01N 2333/185
See application file for complete search history.

(56) References Cited

U.S. PATENT DOCUMENTS

2018/0368743 A1* 12/2018 Lin ..................... H01L 29/1606

* cited by examiner

*Primary Examiner* — Jennifer Wecker
*Assistant Examiner* — Michael Paul Shimek
(74) *Attorney, Agent, or Firm* — Thorpe North & Western, LLP

(57) ABSTRACT

A field effect transistor (FET) biosensor for virus detection of a selected virus within a sample volume is disclosed. The FET comprises a semiconductor substrate, a source and drain electrode on the substrate, the electrodes spaced to form a channel. A gate electrode carried on the substrate and located in the channel between the source and drain electrodes. An insulating layer is coupled to a top surface of the gate electrode and a bottom surface of the source and drain electrodes, with an open channel above the insulating layer. A channel material is coupled to the insulating layer. Aptamers are oriented within the open channel to bind to the channel material and with the selected virus to enable a detection of the selected virus by the FET biosensor based on a change in drain-source current at a selected gate voltage.

8 Claims, 36 Drawing Sheets

| Device: | Zika/aptamer/AuNP channel (p-type) | | Zika/apt./Au film/ (n-type) | | Zika/apt./zeolite/ (n-type) | |
|---|---|---|---|---|---|---|
| Channel Conductance | Aptamer (alone) | Apt./AuNP | Zika/AuNP/apt. | Apt./Au film | Zika/apt./Au film | Apt./zeolite | Zika/zeolite/aptamer |
| $G_{ch}(V_g = -3V)$ | 15.6 | 437 | 3.7(C) | 14E-03 | 0.17 | 0.144 | 4.6 |
| $G_{ch}(V_g = 0V)$ | 8.31 | 3.69 | 0.8 | 7.2E-03 | 0.14 | 0.14 | 15.2 |
| $G_{ch}(V_g = +3V)$ | 5.16 | 45.8 | 0.153 | 18E-03 | 0.21 | 0.1 | 28.6 |
| $G_{ch}(-3)/G_{ch}(3)$ | 3 | 10 | 24(C) | 0.8 | 0.8 | 1.4 | 0.2 |

FIG. 6

WHOLE VIRUS QUANTUM MECHANICAL TUNNELING CURRENT AND ELECTRONIC SENSORS

RELATED APPLICATION(S)

This application claims priority to U.S. Provisional Application No. 62/926,376 filed Oct. 25, 2019 and U.S. Provisional Application No. 63/021,605 filed May 7, 2020, which are each incorporated herein by reference.

GOVERNMENT INTEREST

This invention was made with government support under grant no. 1931100 awarded by the National Science Foundation. The government has certain rights in the invention.

BACKGROUND

As the world population increases and becomes more mobile, the ability to transmit viruses between people and populations has also increased. In addition, the increase in population has amplified the number of interactions between humans and other species of animals that typically live in the wild. The increase in interactions between humans and wild animal species has also increased the transmission of viruses. Most viruses do not cross boundaries between different types of species. However, mutations in viruses can enable a virus to cross a species boundary. When this occurs, the virus is new to a species and can be more deadly since the species' immune system has not developed the ability to defend against the new virus.

Coronaviruses are a group of RNA viruses that cause diseases in mammals and birds.

In humans and birds, they cause respiratory tract infections that can range from mild to lethal. More lethal varieties of coronaviruses can cause SARS, MERS, and COVID-19. The frequency of cross-species transmission of potentially deadly viruses, such as coronaviruses, appears to be increasing.

Two factors can determine the severity of a cross-species transmission of a new virus. The first factor is the transmission rate, also called $R_0$. When $R_0$ is greater than 1, the value infers that an infected person will infect, on average, one more person. When the $R_0$ value for a selected virus is less than 1, then the selected virus usually dies off in a population. However, when the $R_0$ level is greater than one, the virus can spread exponentially in a population. With world travel at an all-time high, a virus can spread across the globe in mere weeks or months.

The second factor is a virus' lethality. Many types of flu viruses kill hundreds of thousands of people each year. The $R_0$ for some flu viruses can be greater than 2, which results in millions of people becoming infected. However, the lethality, or mortality rate of most types of flu is around 0.1%. Those that die of the flu also often have underlying medical conditions which, when combined with the flu, can cause death. These conditions are referred to as comorbid conditions, such as obesity, age, heart conditions, cancer, diabetes, and so forth.

When a new virus, referred to as a novel virus, infects a population, a lack of previous exposure to the population's immune system can result in a higher lethality rate. When a novel coronavirus has a high $R_0$ and a high lethality rate, it can result in a rapid spread in a population and quickly result in a high death rate. The death rate can increase as hospitals fill up and the population's healthcare infrastructure becomes overwhelmed. Millions of people can die in a relatively short time period.

The severe acute respiratory syndrome coronavirus 2, referred to as SARS-CoV-2 (CV2), a novel coronavirus that entered the human population around the end of 2019, resulted in a pandemic with relatively high mortality rates due to the unexpected volume of patients in critical condition. Healthcare systems were flooded as hospitals were not prepared for the number of individuals that needed intensive care. The inability to rapidly scale up testing resulted in worldwide infections of hundreds of millions of people. Many cities and countries were shut down while they attempted to reduce the number of infected individuals and hospitalized patients.

One way to limit the number of infections, and therefore deaths, is to identify who has become infected with the novel virus. This information can then be used to determine any people that those that are infected may have come in contact with. These people can then be quarantined. Rapid and successful quarantining can be used to significantly decrease the $R_0$ level. If the $R_0$ level can be reduced below 1, the virus can be eradicated from the population over time.

When a novel virus, such as a coronavirus, is introduced into a new population, there is typically no way to detect the virus. Standard virus detection means have to be developed for each new virus. The accuracy of virus detection is critical, as it can be expensive for people in a population to quarantine. False positive tests can result in excessive quarantining. In addition, false negative tests can result in additional spread of the virus in the population.

Standard virus detection means can be expensive, time consuming, and slow. In addition, when a novel virus is detected, it can take significant time (weeks or months) to scale up newly developed tests to enable testing of a large population. The challenges associated with development and production of large-scale testing for a novel virus can result in hundreds of thousands of deaths.

An increased ability to quickly develop, produce, distribute, and conduct testing for novel viruses is desperately needed. Such an ability could allow the rapid detection of infected individuals when a novel virus transmission occurs to a new population. If the infected individuals are quickly detected and quarantined, the cost to a society is relatively small. The ability to rapidly and inexpensively test for a novel virus can help ensure that even a novel virus with a high $R_0$ and a relatively high lethality can be detected and eradicated from a population before exponential spread makes eradication difficult. Without such a means, the exponential growth of a novel virus can cost nations trillions of dollars and millions of lives.

Viruses can have residual positive or negative charges. This charge can be detected by specialized detectors to identify when a virus is present. The potential produced when the virus bonds with sensitive and functionalized surfaces of a sensor can also be measured to detect the virus. Other signals can also be monitored in these sensors and related such as the current through the virus or changes in the electromagnetic properties of regions containing the virus. In these cases, parameters such as the refractive index, extinction factor, and dielectric function are measured to detect the virus. The virus's residual charge can also be used to electrostatically manipulate it inside a sensor for chemical bonding or for repulsion. The specialized detectors typically require high tech laboratory type equipment and conditions to provide accurate measurements.

SUMMARY

Electrical sensors can be configured to provide rapid and accurate detection of a biological material in a sample. With a suitable molecular recognition group, almost any virus, bacteria and pathogen can be detected using the electrical sensors. Sensor surfaces on the electrical sensors can be functionalized to bind with molecular recognition groups. For example, aptamers with a thiol end group can be used that readily attach to gold and other metals on sensor surfaces.

Electrical sensors are disclosed that can detect a change in current versus voltage to identify when a selected type of virus attaches to a molecular recognition group. In one embodiment, an insulated gate field effect transistor can be used with different types of channel material to attach the molecular recognition group to an open channel. In another embodiment, a quantum tunneling current can be used to detect when viruses attach to molecular recognition groups in a nano air-gap. In another embodiment, a paper based biosensor can be formed with printed electrodes. The paper based biosensor can be inexpensively manufactured and used by inexperienced users to rapidly and accurately detect virus in a sample. In contrast to PCR and other gold standards for sensing viral particles using their genetic code, the electrical sensors discussed here detect the whole virus without lysing or decomposing them into their RNA, DNA or proteins. The electrical sensors are faster but lack accuracy of the PCR tests. However, since the electronic sensors provide results in under a few minutes, they can be applied many times in the span of time that takes for the PCR results to become available. Using the rapid sensor on the same person frequently, increases the effective accuracy of the sensor. If for some reason, the sensor does not detect the virus initially, over 5-6 trials, the detection events will increase by the number of trials.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 6 is a table showing channel conductance for various gate voltages and channel types;

FIG. 9a is a quantum tunneling current versus voltage for various nano air-gap conditions in the TCS of FIG. 8a;

FIG. 9b is a graph of a change in current per change in voltage for various nano air-gap conditions in the TCS of FIG. 8a;

Figure 1A:
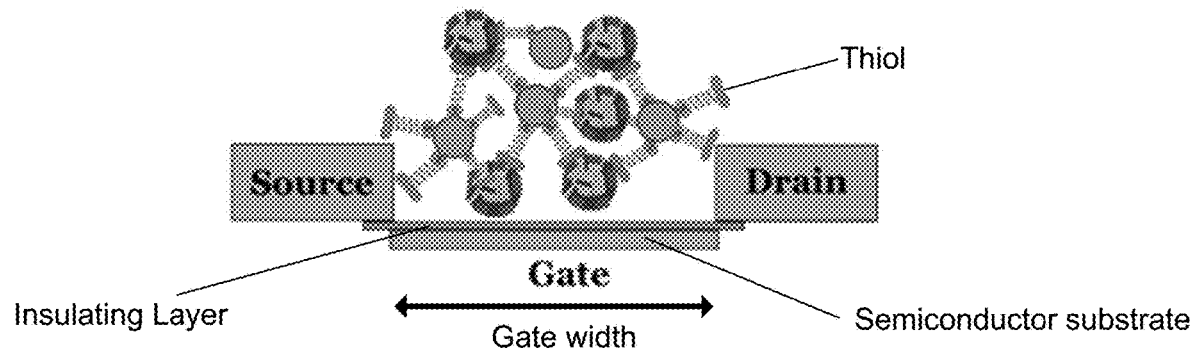
FIG. 1a is a schematic view of an open face field effect transistor (FET) with an aptamer, gold nanoparticle, and Zika virus linked in an open channel of the FET.

FIG.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Electrical Biosensors

An embodiment of the present invention is an easy-to-use, point-of-care, self-administered electrical virus sensor (VS) that can be used to accurately diagnose and assess an infection in individuals. In addition, the stage of infection in the individuals may also be assessed. The electrical sensor can be functionalized with molecular recognition groups that bind with a specific virus's spiking proteins or other pathogens and viral biomolecules. TCSs have single virus limit of detection (LOD) and a sensitivity as high as 95%.

Viral biomolecules can be any chemical entity which is directly or indirectly related to the presence of viruses by indicating a current or previous infection with the virus. Non-limiting examples of viral biomolecules can include whole virus, antibodies, antigens, viral proteins, viral RNA, viral DNA, viral biomarkers, and the like. The following principles can also be applied to other pathogens such as bacteria and the like.

Molecular recognition groups can be any chemical compound or group that selectively binds with the target virus or other pathogens. Non-limiting examples of molecular recognition groups can include aptamers, antigens, antibodies, and the like. Molecular recognition groups can generally include a surface bonding group and a virus binding group. Metal surfaces can be bonded with aptamers, antigens, antibodies, or other molecular recognition groups using any suitable functionalization technique. Further, metal surfaces can optionally be first prepared or activated via functionalization with an active group which binds with a corresponding end of the molecular recognition group. For example, a thiol group can be attached to the metal surface. However, in many cases, the molecular recognition group can include a surface bonding group which directly bonds to the metal surface. Non-limiting examples of surface bonding groups can include organosulfur thiols such as alkyl thiols, dialkyl disulfides, etc. Metal, e.g. gold, surface can also be functionalized via techniques such as, but not limited to, oligonucleotide functionalization via thiol groups, surface saturation with single stranded oligonucleotides, PEGylation optionally including thiol or azide bonding groups, photonic immobilization, azide functionalization, and the like. For some details on the known synthetic functionalization techniques, see INNOVACOAT Gold coatings; Polo E. et al. (2013) *Tips for the Functionalization of Nanoparticles with Antibodies*. In: Guisan J. (eds) Immobilization of Enzymes and Cells. Methods in Molecular Biology (Methods and Protocols), vol 1051. Humana Press, Totowa, N.J. pp. 149-163; Tiwari et al. Nanomaterials 2011, 1(1), 31-63, *Functionalized Gold Nanoparticles and Their Biomedical Applications;* which are each incorporated herein by reference. For example, thiols can be functionalized at one or both ends of an aptamer, an antigen, or an antibody.

In a specific example, the aptamers can include a thiol end group configured to bind with gold electrodes. Thiol end groups bind with almost any materials. Thiol end groups are very aggressive and in some cases may cause corrosion of some metallic surfaces. In those cases other functional end groups with lower binding energies can be used such as, but not limited to, metal-carbon (e.g. carbene, acetylide, vinylidene, etc), metal-nitrogen (e.g. nitrene, etc), azides, and the like.

Formation of a layer of molecular recognition groups can be performed using liquid phase deposition. A molecular recognition group (e.g. aptamer) solution can be applied to the surface in order to bond with the surface. The functionalized group can then react with the exposed surface to bind the molecular recognition groups to the surface. Residual unreacted materials can be removed by washing or evaporation.

The term aptamer stems from the Latin terms "aptus," meaning to fit, and "meros," meaning part. Aptamers are short, single-stranded DNA or RNA (ssDNA or ssRNA) molecules that can selectively bind to a specific target, including proteins, peptides, carbohydrates, small molecules, toxins, and even live cells. Aptamers can assume a variety of shapes due to their tendency to form helices and single-stranded loops. They are extremely versatile and bind targets with high selectivity and specificity.

An aptamer can be developed to attach to a specific target, such as a CV2 virus, a MERS virus, or another desired target. Suitable aptamers can be formed using any technique such as, but not limited to, SELEX (systemic evolution of ligands by exponential enrichment), RAPTAMER, modified SELEX, SELCOS, MAWS, JAWS, and the like. The aptamer can then be manufactured and attached to a virus sensor. A sample from an individual can be tested using the virus sensor. The sample may be a fluid taken directly from the individual, such as saliva, blood, sweat, a stool sample, and so forth and deposited directly on the sensor or placed in a solution and then deposited on the sensor. In addition, the sample may be processed to concentrate any potential virus. For example, polymerase chain reaction (PCR) can be used to concentrate a sample from a nasal swab.

An electronic virus senor that is functionalized with an molecular recognition group can provide rapid and accurate results that are easy to interpret, is easy to use, and can minimize the risk of exposure for healthcare personnel. The virus sensor can be relatively inexpensive and mass manufacturable to enable cities, states, and countries to stockpile the sensor. This can enable rapid testing and detection of a novel virus when it is first introduced into a population. The infected can be quarantined before the virus becomes widespread, thereby limiting the amount of disease, death, and the enormous cost to the society.

Field Effect Transistor Detector

In one example, an open channel insulated gate field effect transistor (FET) device structure can be used to detect a viral biomolecule using an molecular recognition group, as illustrated in FIG. 1a. In this example, the FET biosensor can be configured for viral biomolecule detection of a selected viral biomolecule within a sample volume. The FET can comprise a semiconductor substrate, as illustrated in FIG. 1a. A source electrode can be carried on the semiconductor substrate, such as silicon, gallium arsenide, germanium, boron, indium, carbon nanotubes, etc. In the example of FIG. 1a, the semiconductor is silicon. A drain electrode can also be carried on the semiconductor substrate. A gate electrode can be carried on the semiconductor substrate and located between the source electrode and the drain electrode, with the gate electrode recessed below the source electrode and the drain electrode to form an open channel. In one example, the source electrode, gate electrode, and drain electrode can be comprised of one or more conductors comprising silver, gold, copper, platinum, aluminum, zinc, cobalt, nickel, tungsten, or ruthenium. The source, drain, and gate electrodes can have a thickness of between approximately 50 nm and 250 nm.

An insulating layer can be deposited on a top surface of the gate electrode and a bottom surface of the source electrode and the drain electrode such that the insulating layer is located between the gate electrode and source electrode and between the gate electrode and the drain electrode. The insulating layer can form a bottom of the open channel. The insulating layer can be formed of an insulating material that can be used as a gate dielectric, including silicon dioxide, hafnium dioxide, nitride-oxide, titanium oxide, or composites thereof. In one example, the insulating layer can have a thickness of approximately 5 nm to 20 nm. A distance between the source electrode and the drain electrode can create a channel width between approximately 500 nm and 2000 nm.

Figure 1B:
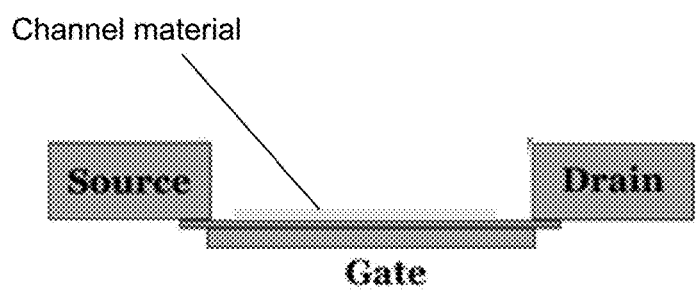
FIG. 1b is a schematic view of the open face FET with channel material in the open channel.

A channel material can be coupled to the insulating layer, as shown in FIG. 1b, such that the sample volume can be oriented within the open channel. The channel material can be a zeolite layer formed in the channel. Alternatively, the channel material can be formed of a thin gold film. In one example, the thin gold film can have a thickness between approximately 20 and 40 nanometers deposited on the insulating layer in the channel.

Molecular recognition groups such as aptamers can be functionally attached to the channel material in the FET of FIGS. 1a and 1b. The molecular recognition groups may be attached to the zeolite material. Alternatively, the thin gold film can be functionalized to attach the molecular recognition groups.

In another example, the channel material can be gold nanoparticles. In this example, the gold nanoparticles have a diameter of approximately 50 nm. However, the diameter can be selected based on the size of the viral biomolecule or molecule that is attached to the molecular recognition group. In this example, the Zika virus is attached to the molecular recognition group, with a diameter of approximately 40 nm. The gold nano particles can have a diameter between approximately 25 nm and 75 nm, with at least a portion of the gold nano particles attached to at least a portion of the molecular recognition groups. Other examples of viruses that can be attached are the SARS-COV-1 virus, the SARS-COV-2 virus, or another coronavirus or other type of virus.

As illustrated in FIG. 1a, the aptamers can be oriented within the open channel, the aptamers configured to bind with the selected viral biomolecule. By depositing the aptamers and viral biomolecule in the open channel on the channel material, it can result in a change in a current ($I_{DS}$) between the drain electrode and the source electrode or a channel conductivity at a selected voltage ($V_{GS}$) that is applied to the gate electrode relative to the source electrode. The change in current or voltage can be used to enable a detection of the selected viral biomolecule by the FET biosensor based on the change in $I_{DS}$ at the selected voltage or the channel conductivity at the selected voltage.

Figure 1C:
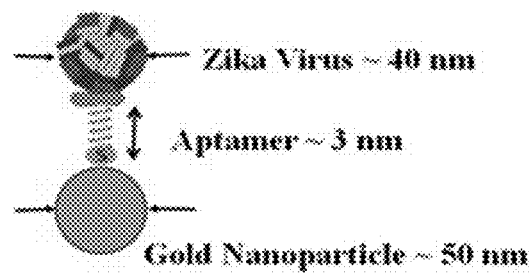
FIG. 1c is a schematic view of a Zika virus linked to an aptamer that is linked to a gold nanoparticle.
Figure 1D:
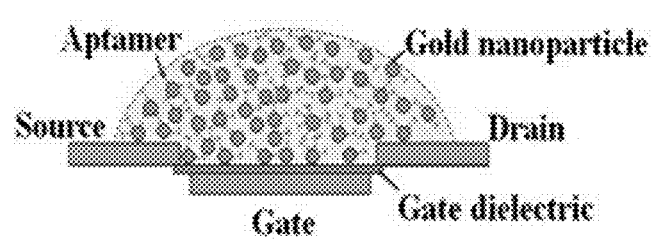
FIG. 1d is a schematic view of a channel filled with aptamer functionalized AuNPs.
Figure 1E:
FIG. 1e is a schematic view of the channel of FIG. 1d with dried aptamer buffer.

The channel between the source and drain can be filled with aptamers with thiol end that bind with AuNPs or any metal substrate, as shown in FIG. 1d. The aptamers can be applied in a buffer that can dry in the channel, as shown in FIG. 1e. In one example, the aptamer buffer solution can have between approximately 0.5 micro Molar (uM) and 5 uM concentration. The virus can then be added in a suspension fluid to the dried aptamer buffer. In another example, at least a portion of the aptamers can be suspended within the open channel in one or more of a dried suspension, a hydrogel, or a dried network of functionalized nanoparticles.

Figure 1F:
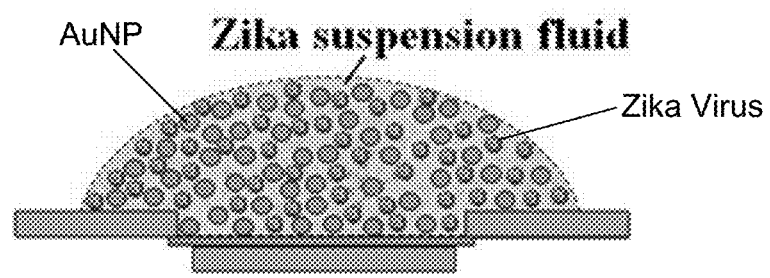
FIG. 1f is a schematic view of the channel of FIG. 1e after a liquid sample including virus is applied to form a virus suspension fluid.

The other end of the aptamer can be functionalized to bind with the virus, such as the Zika virus's capsid protein, as shown in FIGS. 1f and 1c. The Zika virus can form a bridge, as shown in FIG. 1a, with the gold nanoparticles (AuNP) combined with the aptamer conjugates when it binds with the aptamer. The binding with the Zika capsid protein is associated with the unfolding of the aptamer and subsequent charge redistribution between the Zika and the aptamer.

Figure 2A:
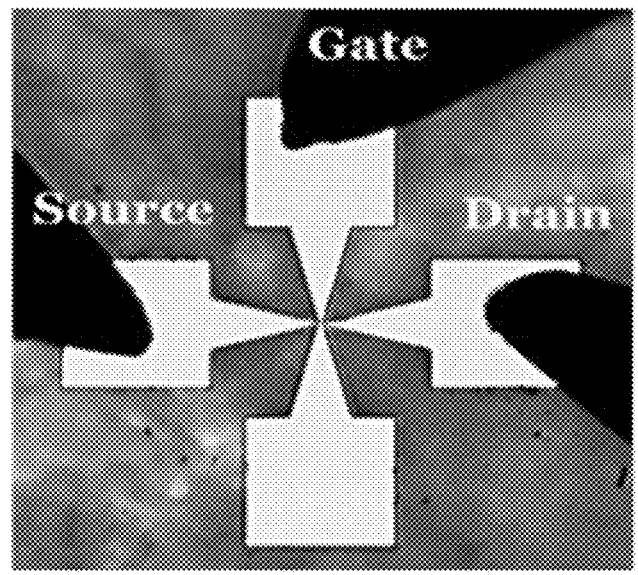
FIG. 2a is an optical image of the open face FET.
Figure 2B:
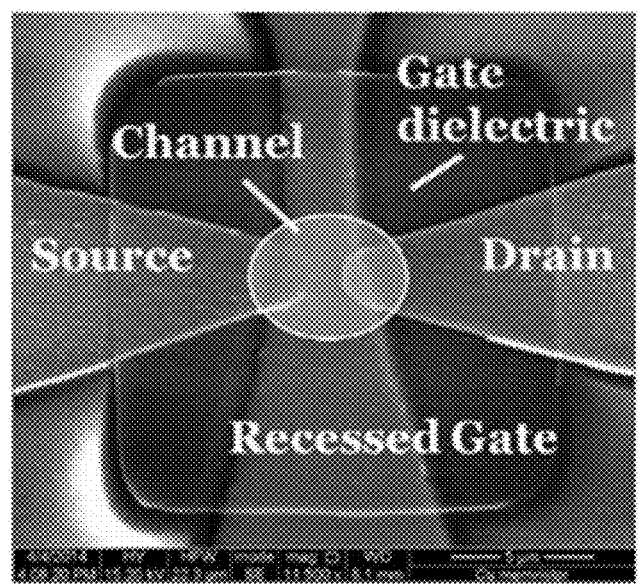
FIG. 2b is a scanning electron microscope (SEM) image of the open face SEM showing the recessed gate and channel.

FIG. 2a illustrates an optical image of an example open channel Insulated Gate FET that can be used to detect a virus using an aptamer. The example of FIG. 2a illustrates a recessed gate with a 10 nm atomic-layer of deposited Hafnium dioxide ($HfO_2$) as the gate dielectric. In this example, the source, drain and gate electrodes are comprised of approximately 100 nm-thick sputtered platinum. The channel length (the distance between the source and the drain) is approximately 1 micrometer (μm). The open face channel with the embedded gate, as illustrated in a scanning electron microscope (SEM) image of FIG. 2b, permits deposition of different channel materials to investigate the field effect on the channel materials that are exposed to the environment. The device geometry, with its exposed channel region enables direct sensing of pathogens, gases, and chemicals.

The channel in the insulated gate FET illustrated in FIGS. 1a-1e and 2a-2b can be functionalized with aptamers that bind with a selected viral biomolecule and provide selectivity to the FET detector. In addition to the aptamers, other channel materials that can be used include gold nano particles (AuNPs), sputtered Au films and zeolite molecular sieves. The zeolite molecular sieves can be used to immobilize the aptamers in the FET channel region, provide a medium for a viral biomolecule to be trapped to bind with the aptamers, and to increase the channel conductivity to measurable values. In this example, the Zika virus was used to determine current vs voltage (I-V) curve. Both Zika and its aptamers are electrically insulating, and an electrically suitable structural material is used to contain the Zika and the aptamers.

Figure 4A:
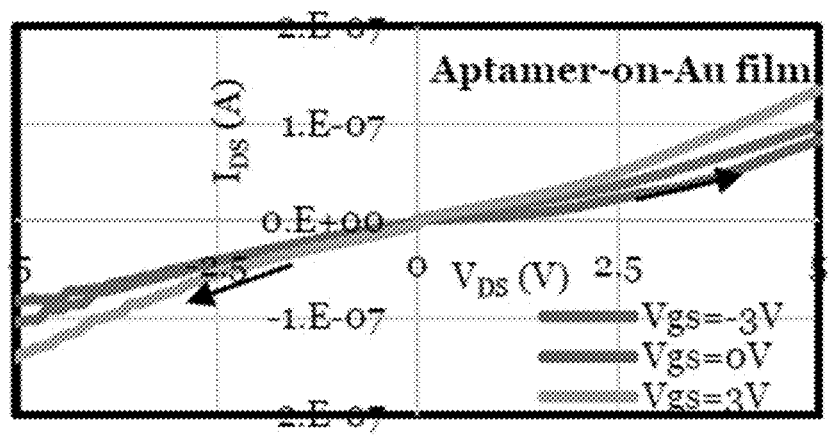
FIG. 4a is a $V_{DS}$ vs $I_{DS}$ graph for selected $V_{gs}$ for the open face FET with an aptamer applied to a thin gold film located in the channel.
Figure 4B:
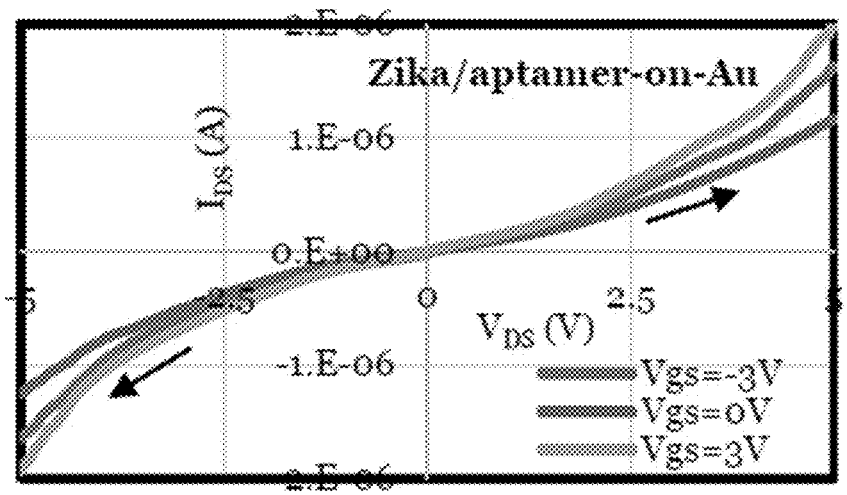
FIG. 4b is a $V_{DS}$ vs $I_{DS}$ graph for selected $V_{gs}$ for the open face FET with Zika bound to an aptamer that is applied to a thin gold film located in the channel.

In one example, experiments were conducted for the FET illustrated in FIGS. 2a and 4b to obtain I-V curves for with each of the three channel materials. The Aptamer in the experiment was a 32 nucleotides-long single-strand chain with one end that is functionalized with a thiol group and the other end that is functionalized with a protein that binds with the Zika's SF9 envelope protein. The stock solution of the Zika virus had a concentration of TCID50/ml liter. The number of Zika viruses present in 1 microliter μl of stock Zika was approximately $1.7 \times 10^8$, as estimated from the SEM images.

As previously discussed, a first type of channel material that can be used is AuNPs, with a diameter of approximately 50 nm. The AuNPs were mixed with 1 μM aptamer in 1:1 ratio by volume to form a colloidal solution. The colloidal solution was heated to 60° C. for 5 minutes.

A second type of channel material for the FET devices is zeolite. In one example, the FET device can be pre-deposited with zeolite. The zeolite can be mixed in acetone and ultrasonicated to form a colloidal solution. The thoroughly mixed colloidal solution can then be deposited, such as drop-casted, on the channel using a pipette. Subsequently, aptamer and Zika viruses can be deposited on the zeolite-covered channel.

A third type of channel material for the FET device is using a sputtered thin gold film. In one example, the thin gold film can have a starting channel resistivity of 3.1 kΩ-cm. The aptamers and Zika viruses can then added to the channel on top of the thin gold film.

In each experiment, the number of aptamers in 1 μl (1 μM) was $6 \times 10^{11}$, and the number of AuNP in 1 μl was $4.5 \times 10^7$. The number of aptamers per AuNP was $1.3 \times 10^4$ and Zika concentration was $1.7 \times 10^8$ Zika/μl.

Experimental Results

Figure 3A:
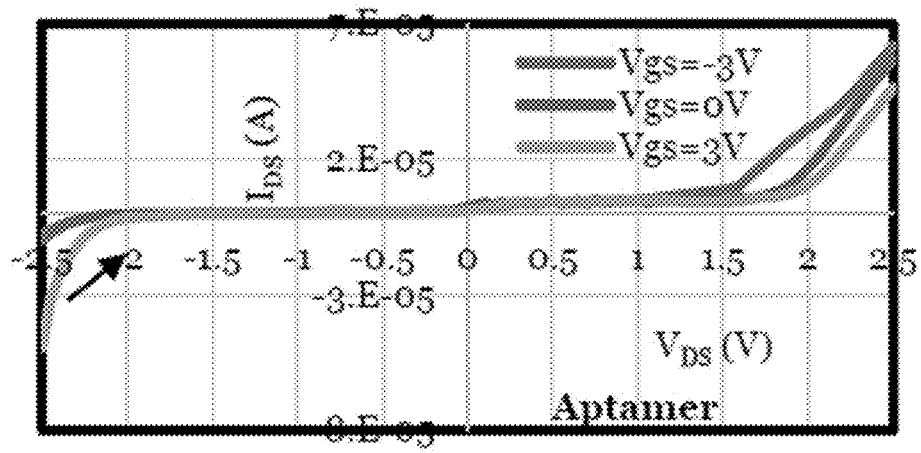
FIG. 3a is a current versus (vs) voltage graph for the drain to source voltage ($V_{DS}$) vs drain to source current ($I_{DS}$) for selected gait to source voltages ($V_{gs}$) applied to the open face FET with an aptamer applied to the channel.
Figure 3B:
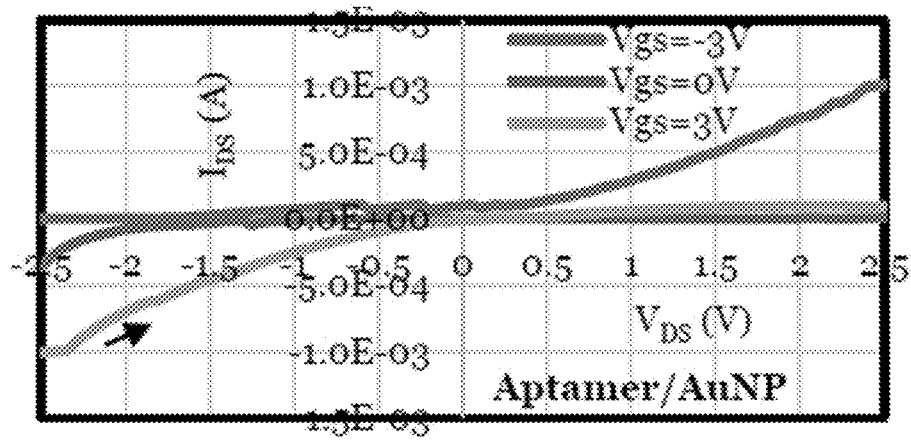
FIG. 3b is a $V_{DS}$ vs $I_{DS}$ graph for selected $V_{gs}$ for the open face FET with an aptamer and gold nanoparticles applied to the channel.
Figure 3C:
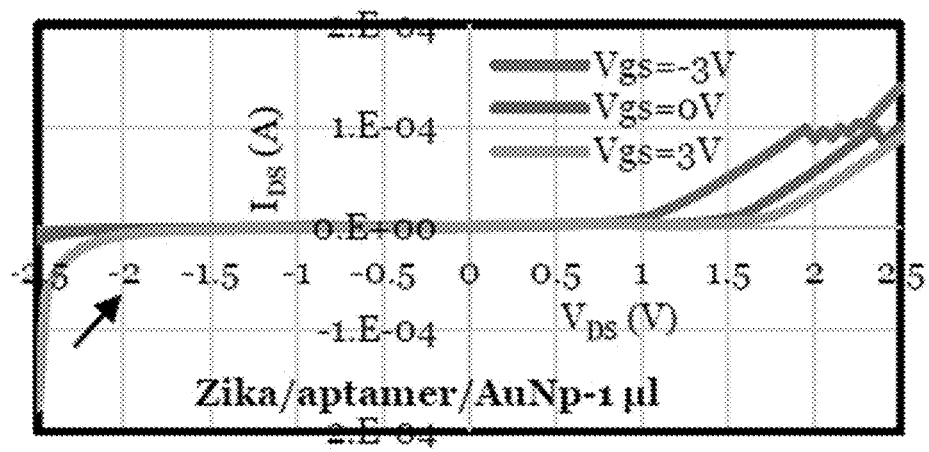
FIG. 3c is a $V_{DS}$ vs $I_{DS}$ graph for selected $V_{gs}$ for the open face FET with an aptamer and gold nanoparticles and Zika virus applied to the channel.

FIGS. 3a-c show a current versus voltage curve for a voltage applied between the drain and source (IDS-VDS) of the open channel FET for different channel materials, including aptamers only (FIG. 3a), aptamers and AuNPs (FIG. 3b), and Zika, aptamers, and AuNP (FIG. 3c). The starting voltage for the IDS-VDS sweeps was from VDS=−2.5 V to +2.5 V. The sweep directions are denoted by the arrows.

Figure 3D:
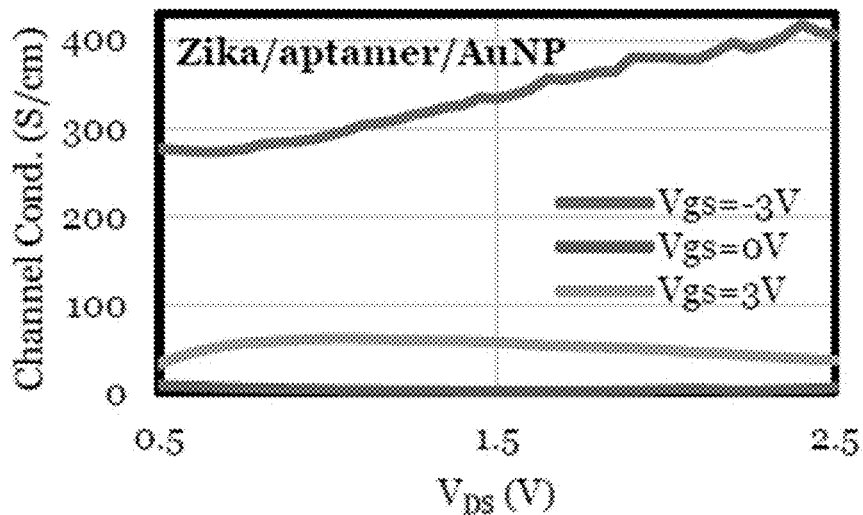
FIG. 3d is a graph of channel conductance over a range of $V_{DS}$ for selected $V_{gs}$ with aptamer and gold nanoparticles and Zika virus applied to the channel.

FIG. 3d illustrates the change in channel conductance, measured in Siemens per centimeter (S/cm) over a change in the drain to source voltage (VDS) at selected gate to source voltages (Vgs) of 3 Volts, 0 Volts, and −3 Volts (V). The relatively low conductivity of 15 S/cm at VDS=2V and Vgs=−3V in the aptamer only channel of FIG. 3a increased to 440 S/cm upon adding AuNP to the aptamers. Gate field-effect also increased. The AuNPs attach with the thiol end of the aptamers with functional ends that attach to SF9 envelope protein of the Zika. The AuNPs have residual positive charges and are attracted to the gate region when the gate voltage is negative. For positive gate voltages, however, the NPs move away from the gate region for Vgs=0V. At Vg=0 V, the only external electric field in the channel is from the drain to the source, such that when it is positive, it repels the positively charged AuNPs towards the source region.

The channel conductivity in FIG. 3d was obtained for the Zika, AuNP, and aptamer channel. The channel conductivity for other devices with aptamer, AuNP/aptamer, Zika/AuNP/aptamer channels are shown in the table in FIG. 6. When Zika is added to the channel, the Zika bonded with the aptamers bridging the aptamer-AuNPs and reduced channel conductivity considerably from 440 S/cm to 3.7 S/cm at $V_{DS}$=2V and Vgs=−3V. The gate field effect clearly showed that the aptamer/AuNP channel is P-type with a relatively large transconductance of 300 microseconds (μS) (VDS=2V) compared to the Zika, aptamer, AuNP channel (also p-type) but with a lower transconductance of 2 μS (VDS=2V).

It is noted that Zika is slightly negatively charged and acts as an n-type channel material. It appears that the positively charged AuNPs become compensated by the negatively charged Zika. Zika also binds with the aptamers on the AuNPs reducing the density of the charge hopping sites and reducing the channel conductivity.

Figure 4C:
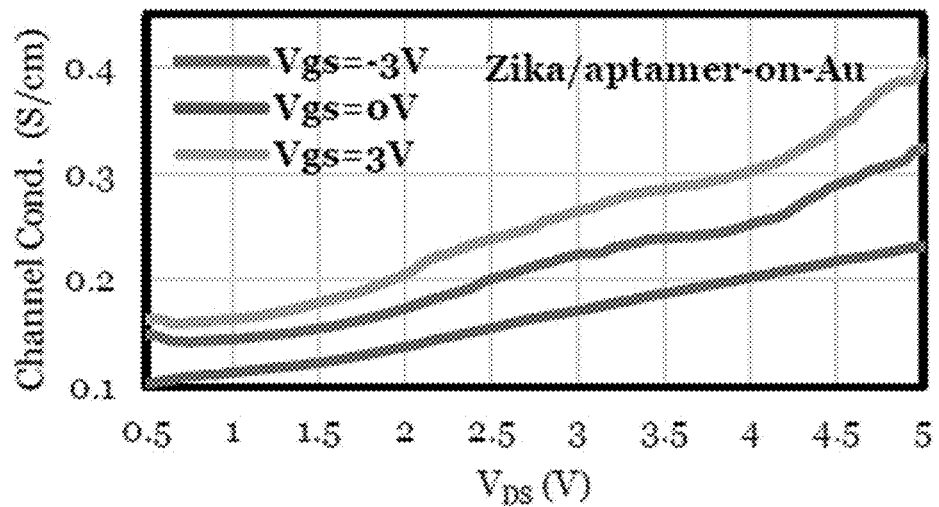
FIG. 4c is a graph of channel conductance over a range of $V_{DS}$ for selected $V_{gs}$ with Zika bound to an aptamer that is applied to a thin gold film located in the channel.

Next in the experiment, the AuNPs were replaced with a thin layer of gold (~30 nm) (the third channel type) that was sputtered in the channel before depositing the aptamer and Zika. FIGS. 4a-b show the FET I-Vs with the thin layer of gold with a resistivity of approximately 3 kilo Ohms per centimeter (kΩ-cm) after depositing the aptamers and then the Zika. FIG. 4a shows the FET $I_{DS}$-$V_{DS}$ curves for the aptamer only. FIG. 4b shows the FET $I_{DS}$-$V_{DS}$ curves for the Zika virus on aptamer. FIG. 4c shows the channel conductivity of Zika/aptamer on the thin layer on gold with different gate voltages (Vgs=−3V, 0V and +3V).

The aptamer with the thiol end group binds with the thin gold layer in the channel and, in most cases increases the drain-source resistance by lifting off some the channel gold. The channel in this case was n-type, opposite of the aptamer/AuNP that was p-type. Subsequently, Zika viruses were added to the aptamer-on-thin gold layer in the channel. The Zika increased the channel conductance by a factor of approximately 10, as can be seen by comparing FIGS. 4a and 4b. The conductivity increased from the aptamer/Au channel (0.02 S/cm) to the Zika/aptamer/Au (0.2 S/cm) at VDS=2V. There was also a corresponding increase in the FET transconductance from 7.3×10-3 µS to 4.5×10-2 µS at VDS=2V. The change in the channel conductivity is shown in FIG. 4c for different gate voltages.

Figure 5A:
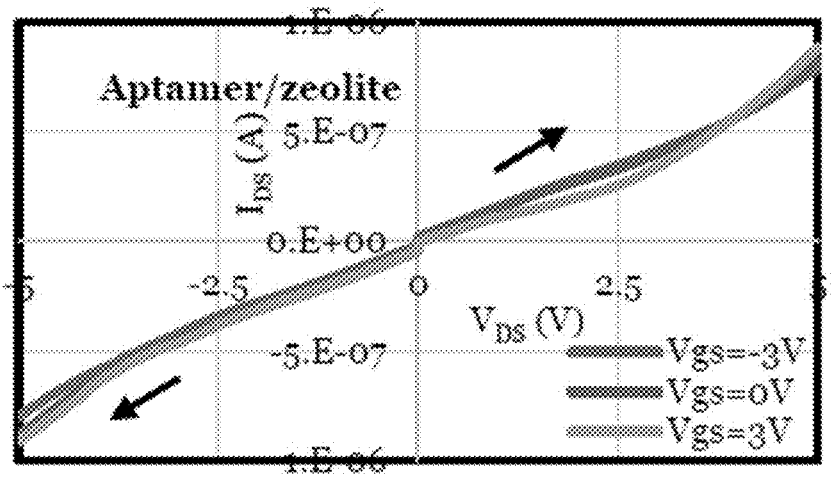
FIG. 5a is a $V_{DS}$ vs $I_{DS}$ graph for selected $V_{gs}$ for the open face FET with an aptamer in zeolite applied to the channel.
Figure 5B:
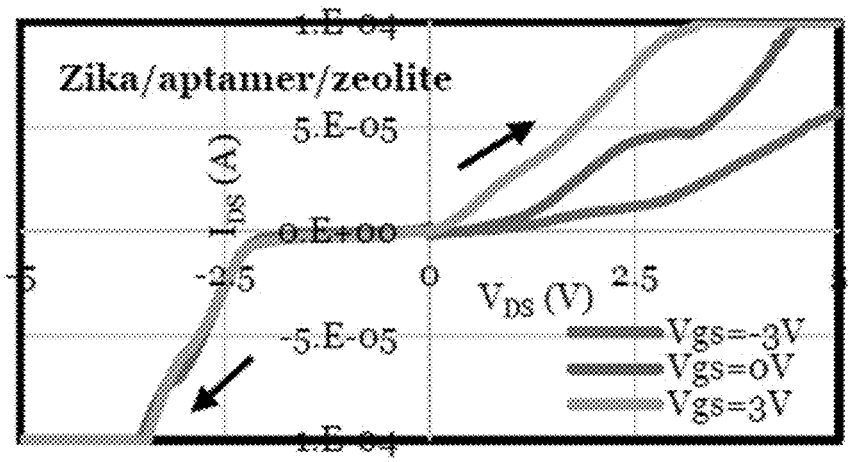
FIG. 5b is a $V_{DS}$ vs $I_{DS}$ graph for selected $V_{gs}$ for the open face FET with an aptamer and Zika in zeolite applied to the channel.
Figure 5C:
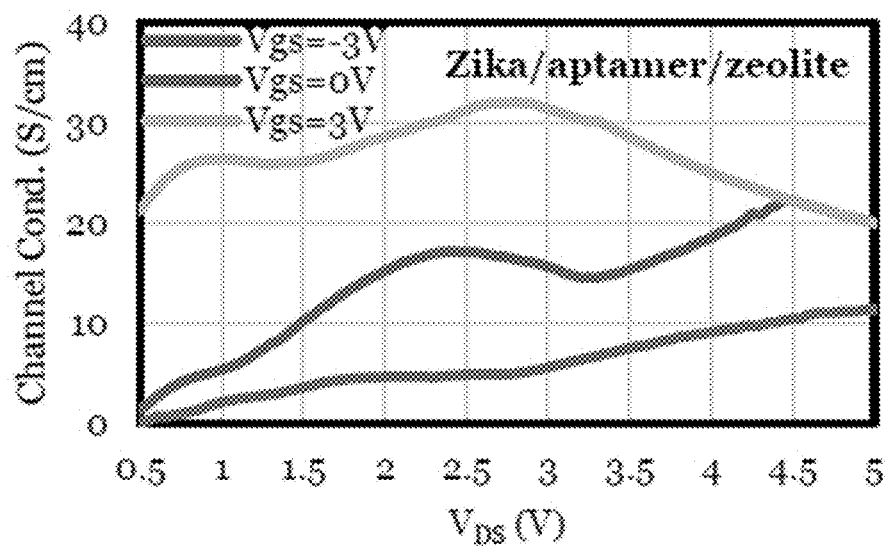
FIG. 5c is a graph of channel conductance over a range of $V_{DS}$ for selected $V_{gs}$ with Zika bound to an aptamer that is applied to zeolite in the channel.

Next, the sputtered gold channel layer was replaced with zeolite that has micro-pores in its structure that can accommodate the aptamer and Zika viruses and situate them in the FET channel region. FIGS. 5a-b show the IDS-VDS for different gate voltages for the zeolite channel material. FIG. 5a shows the FET $I_{DS}$-$V_{DS}$ curves for aptamer in zeolite. FIG. 5b shows the FET $I_{DS}$-$V_{DS}$ for Zika in aptamer zeolite FIG. 5c shows the channel conductivity of Zika/aptamer/zeolite for different gate voltages (Vgs=−3V, 0V and +3V)

The channel conductivity in this case increased from 0.1 S/cm to 28.6 S/cm after adding aptamer and Zika. There was also a corresponding increase in the device transconductance from 2.4×10-2 µS to 9 µS. FIG. 6 is a table that lists the conductivities for different channel materials. The channel in the case of the zeolite channel device acted as an n-type material, similar to the thin layer of gold that was sputtered on the FET. The gate field effect was only noticeable for positive $V_{DS}$. The Zika/zeolite/aptamer channel showed a relatively large gate field effect as can be seen in FIG. 3c. However, the largest gate field effect was observed in the AuNP-based channel, as shown in the table in FIG. 6.

Figure 7:
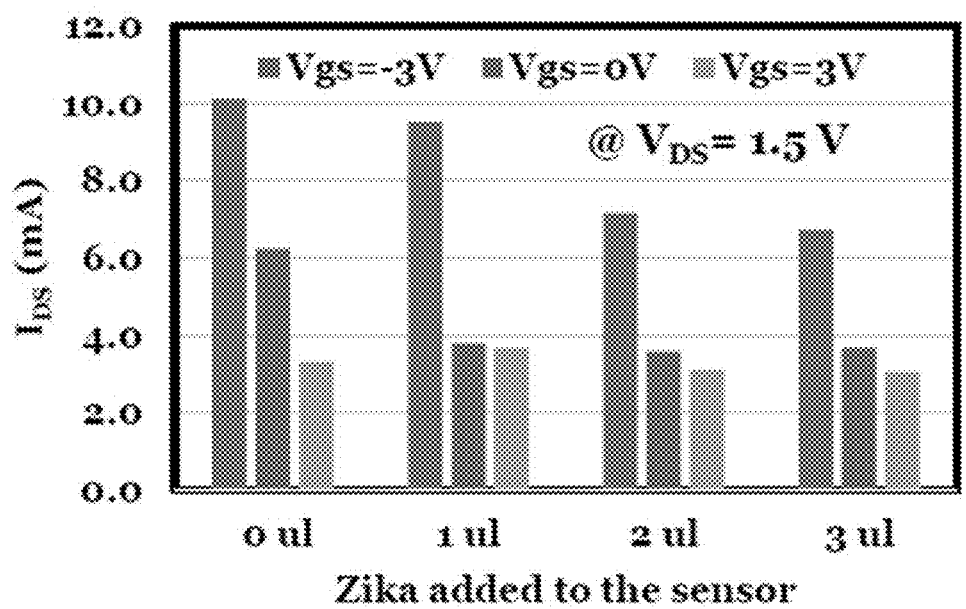
FIG. 7 is a $V_{DS}$ vs $I_{DS}$ graph for selected $V_{gs}$ for the open face FET with selected amounts of Zika added to the channel.

The FET biosensor sensitivity (SFB) is defined as: SFB=$\Delta V_{out}/\Delta C_{Zika}$ that is proportional to $\Delta I_{DS}/\Delta C_{Zika}$, where $V_{out}$ is the sensor output voltage and $C_{Zika}$ is the Zika concentration. FIG. 7 shows the $I_{DS}$ of the Zika/aptamer/AuNP device at 3 different gate voltages as a function of Zika concentrations at a $V_{DS}$ of 1.5 V. While the largest sensitivity for the device used in these experiments was obtained at Vgs=0V going from zero Zika to 1 µl of Zika, the gate voltage of −3 V produced largest sensitivity going from 1 µl of Zika to 2 µl of Zika. Since the sensor sensitivity changes as a function of Zika concentration, this data also shows how gate voltage can be used to increase the sensor dynamic range.

In the experiments, FET $I_{DS}$-$V_{DS}$ curves were measured for the three different channel types of AuNPs, thin gold film, and zeolite. The gate field effect was then used to determine channel conductivity type and to enhance the FET sensors' sensitivity. The gate field effect clearly showed that the aptamer/AuNP channel is p-type with a relatively large transconductance of 300 µS (VDS=2V) compared to the Zika/aptamer/AuNP channel (also p-type) but with lower transconductance of 2 µS (VDS=2V). There was large amount of charge trapping (~1015 cm2) in the Zika/aptamer/AuNP channel. The Aptamer/Au and the aptamer/zeolite channels were both n-type and their conductivities increased when Zika was added. A combination of AuNP and zeolite biosensing FETs can be used to design complimentary bio-FET sensors. It was shown that the gate voltage in FET biosensors can be used to increase their sensitivity.

An advantage of FET sensors with pathogen/virus as their active channels is the ability of their gate field effects in enhancing their sensitivity and selectivity.

Tunneling Current Sensor

In one example embodiment, the electrical viral biomolecule sensor can comprise one or more quantum-mechanical tunneling current sensors (TCS). The TCS can be functionalized to bind with aptamers. A sample from an individual can be introduced to the TCS. If a virus is in the sample, it will bind with the aptamer and the TCS can identify that binding has occurred in near real time. This can enable an infected individual to be rapidly detected and quarantined before the novel virus can spread in a population.

As a general matter, a vertical nano gap tunneling current biosensor can comprise a first electrode oriented on a semiconductor substrate. The first electrode can be configured to be connected to a parameter analyzer. The first electrode also has a conductive sample surface including molecular recognition groups attached to the surface which are configured to bind with a selected virus. More specifically, the same principles described throughout with respect to the molecular recognition groups can be applied in this sensor variation. The sample surface can have an open region located above the first electrode such that the a sample can be introduced onto the surface from outside of the biosensor. A second electrode is also spaced from the first electrode with a portion of the electrode protruding into the open region to form a nano-gap between the first electrode and the second electrode. The nano-gap spans the tunneling gap distance to enable a tunneling current between the first electrode and the second electrode when a voltage differential is provided between the first electrode and the second electrode. A dielectric layer can also be used to separate the first electrode and the second electrode. The parameter analyzer can be configured to detect a change in the tunneling current through the nano-gap over a range in voltage and the change in the tunneling current is used to identify when the selected virus is bound to the molecular recognition groups. Typically, the tunnel gap distance is also orthogonal to a plane of the conductive sample surface (see FIG. 8a as an example).

The semiconductor substrate can comprise any suitable semiconducting material such as, but not limited to, silicon, gallium arsenide, germanium, and the like. An optional passivation layer can be oriented between the semiconductor substrate and the first electrode. Non-limiting examples of a passivation layer can include Si3N4, oxides or nitrides. Notably, in this case the dielectric layer can also act as a passivation layer. Additional optional intermediate layers can also be used, for example to reduce lattice mismatch and delamination depending on the semiconducting, electrode and dielectric materials.

The vertical nano-gap tunneling current biosensor can be particularly adapted to detection of either SARS-CoV-2 or ZIKA. Although other conductive materials such as copper, platinum, palladium, silver, etc, can be used gold can be particularly useful in forming the first and second electrodes. The dielectric layer can be any suitable electrically insulating layer. Non-limiting examples of suitable dielectric layer material can include silicon dioxide, high-κ gate dielectrics, and low-κ gate dielectrics. The vertical nano-gap tunneling current biosensor can further include a hydrophobic layer coated on a top surface of the second electrode. For example, a hydrophobic resist can be coated along a top surface in order to prevent liquid sample materials during use or during deposition of the molecular recognition groups on the sample surface. Regardless, the tunneling gap distance can be formed to have a selected gap size based on the selected virus.

Figure 8A:
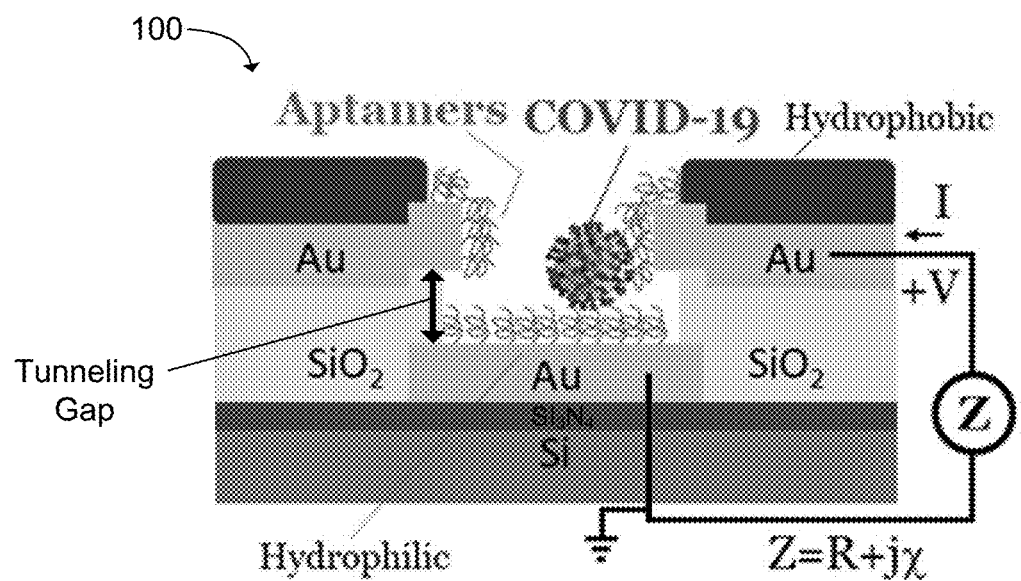
FIG. 8a is a schematic view of a tunneling current sensor (TCS) with aptamers attached to a gold surface in a nano air-gap sized for a Covid-19 virus.

One specific example of a vertical gap TCS 100 is illustrated in FIG. 8a. The TCS is comprised of electrodes that are separated by a tunneling gap that is tuned to match the size of a desired virus and/or molecules that the TCS is tuned to sense. Each TCS is functionalized with different molecular recognition groups to bind with a selected virus, such as CV2, biomarkers, antibodies, or other desired molecules.

The TCS is comprised of a silicon layer configured to carry one or more TCS. In one example, an array of tens, hundreds, or thousands of TCS can be etched onto the silicon layer, as illustrated in the example of FIG. 8c. Each sensor in the array can be formed with a tunneling gap between the top electrode and the bottom electrode. The tunneling gap of each sensor in the array can be formed to have a desired gap size based on the type of virus, biomarker, antibody, or molecule that is to be sensed. For example, a tunneling gap for a virus, such as CV2, may have a gap size of approximately 140 nanometers (nm), based on a size of the virus. In this example, CV2 has a diameter of approximately 125 nm. Alternatively, the Zika virus has a diameter of approximately 40 nm. A tunneling gap of approximately 70 nm can be sufficient to detect the Zika virus. A tunneling gap for a biomarker or antibody may have a gap size of approximately 1-5 nm.

In one example, the TCS 100 can be formed by the deposition of a 100 nm $Si_3N_4$ layer on 4" Silicon using a low-pressure chemical vapor deposition (LPCVD) technique. The next step is the sputter deposition and patterning (using a first mask) of a first gold/chromium (AU/CR) layer (100 nm thick) to form the bottom electrode and its pads for wire binding. The next step is to deposit the spacer SiO2 layer using sputtering or the atomic layer deposition technique (for narrow gaps in antibody and biomarker sensors) followed by annealing at 400 Celsius (C) in forming gas. The spacer layer thickness will be 140 nm for the CV2 virus, and 2-5 nm for the biomarkers and/or antibody detection depicted in FIG. 8b. Next, a second Au/Cr layer (100 nm thick) can be sputtered and patterned using a second mask to produce a top electrode and its connecting pads. A photoresist and the patterned Au/Cr layer can then be used as a mask to dry etch the spacer SiO2 layer to form the air gap. The last fabrication step is to deposit a top insulating layer of photoresist (hydrophobic) and pattern it with a third mask to cover the whole chip and only expose the active part of the devices (hydrophilic) and the wire bonding pads.

The hydrophobic sensor array surface can be hydrophobic to guide a virus sample, such as saliva, to reside in the active hydrophilic channel (dry-etched SiO2 and treated with oxygen plasma) of the TCS. The aptamers can be attached to a thiol end group. The gold electrodes can be treated with oxygen plasma to increase their binding energy with the thiol end group of the aptamers. The TCS array can have an excellent LOD/sensitivities. Machine learning software can be developed to address device-device variations and sensor drift commonly observed in biosensors.

Figure 9A:
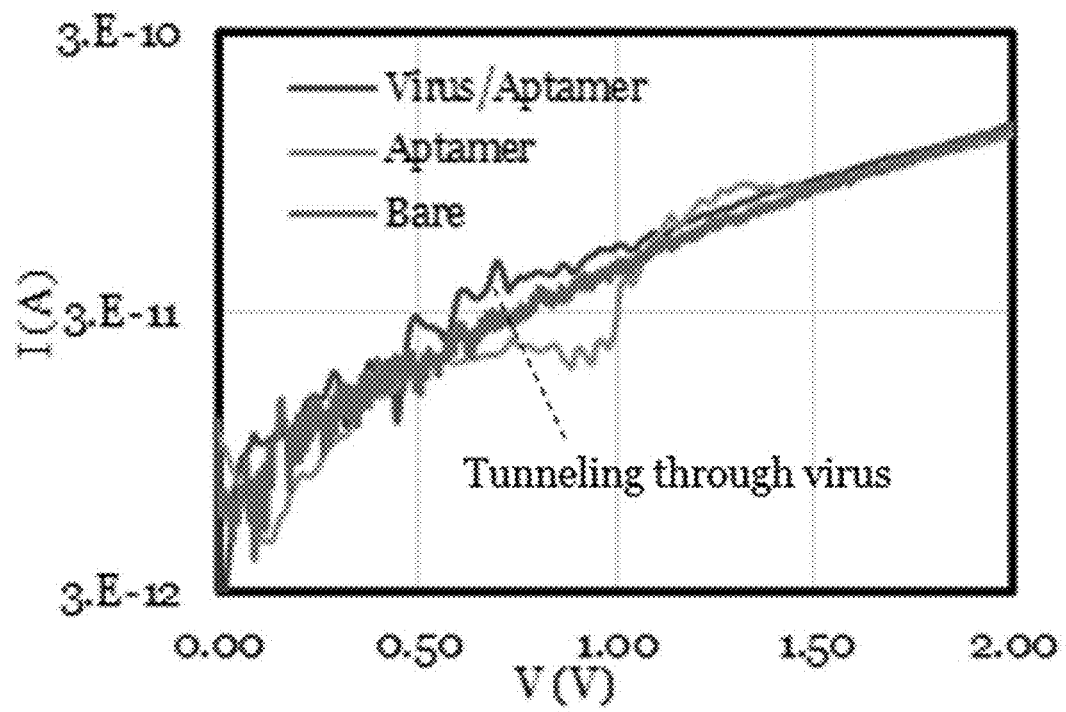
Figure 9B:
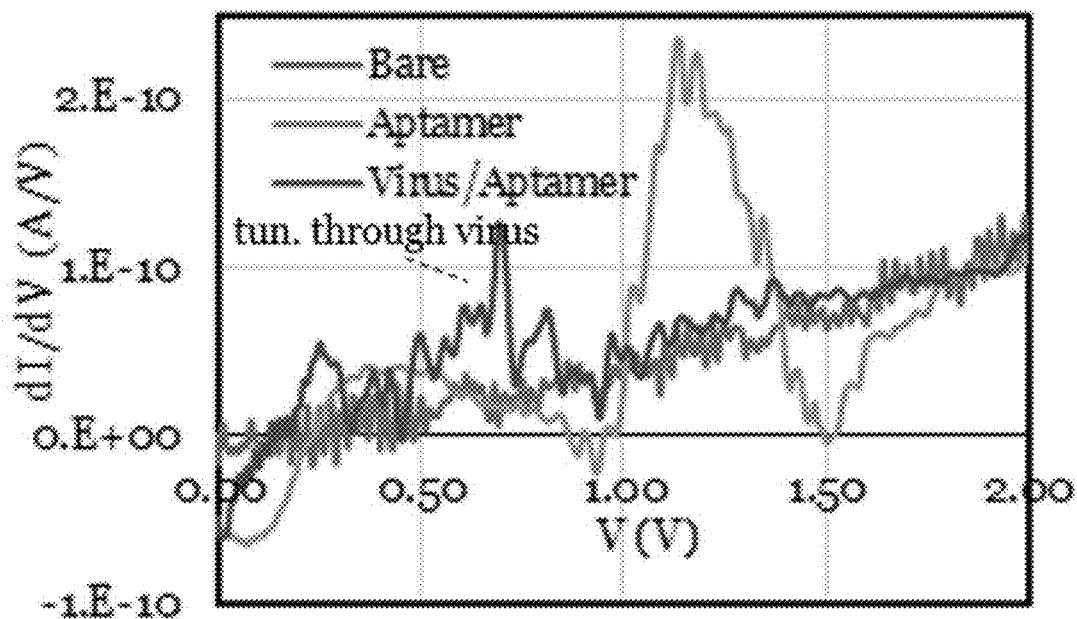

A voltage can be applied between the electrodes in the TCS and a complex impedance Z can be measured to determine the current and voltage characteristics of the TCS both before and after the aptamer and molecule (i.e. virus) sample is applied to the air gap in the one or more TCS in an array. FIG. 9a illustrates a quantum tunneling current versus voltage characteristics of a micro-fabricated TCS. FIG. 9b illustrates the differential current versus voltage of a tunneling gap current sensor (TCS) with and without the aptamer, and aptamer/virus. The current and differential current versus voltage characteristics of the tunneling gap device are uniquely determined by the effective band diagram of the highest occupied molecular orbital and lowest unoccupied molecular orbital (HOMO-LUMO) of the gold-aptamer-CV2-aptamer-gold device. The I/V and differential current versus voltage curves can be used to identify when a molecule or virus has attached to an aptamer on the TCS. This will be further discussed in the following sections.

TCS Theoretical Considerations

Figure 10A:
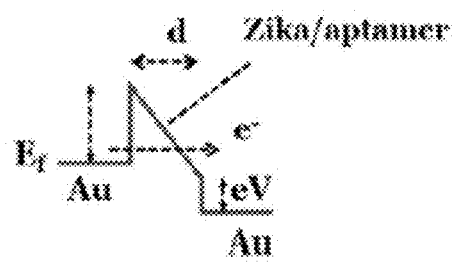
FIGS. 10a-d are graphs of energy band diagrams of different tunneling conduction mechanisms including: a) Fowler-Nordheim tunneling; b) direct tunneling; c) trap assisted tunneling; and d) Different mechanism of for subthreshold leakage current conduction with TE: thermionic emission, TFE: Thermionic field emission, FE: Field emission or field induced charge generation and defect induced field emission.
Figure 10B:
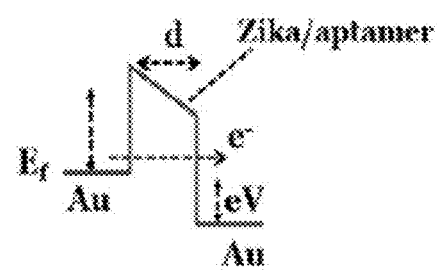
Figure 10C:
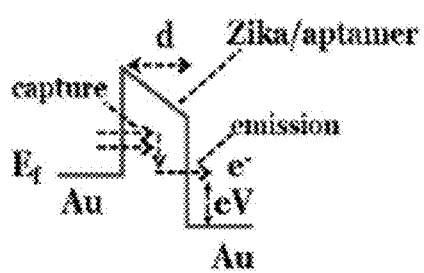

The current versus voltage characteristics of the tunnel junction sensor has leakage current regions at sub-threshold voltages followed by exponentially increasing current (I) regions when the junction voltage (V) exceeds the threshold voltages both in the forward (VT+) and reverse (VT−) bias directions. The current can exhibit different voltage dependence depending on the electron tunneling mechanisms schematically shown in FIGS. 10a-d. These mechanisms include Fowler-Nordheim tunneling, as shown in FIG. 10a, $$\left(I \propto V^2 \exp\left[-\frac{4d\sqrt{2m^*(q\phi_B)^3}}{3q\hbar V}\right]\right),$$

where d is the barrier thickness, $\phi_B$ is its height, m* is the effective mass of electrons in the barrier, q is the electronic charge, h is the modified Plank's constant, and V is the applied voltage), trap assisted tunneling current (FIG. 10c)

$$\left(I \propto q \int_0^d \frac{N_T(x)}{\tau_c(x) + \tau_e(x)} dx,\right.$$

where $N_T$ is the trap concentration and $\tau_c$ and $\tau_e$ are trap capture and emission time constants, respectively), and direct tunneling (FIG. 10b)

$$\left(I \propto V \exp\left[-\frac{2d\sqrt{2m^*q\phi B}}{h}\right]\right).$$

Figure 10D:
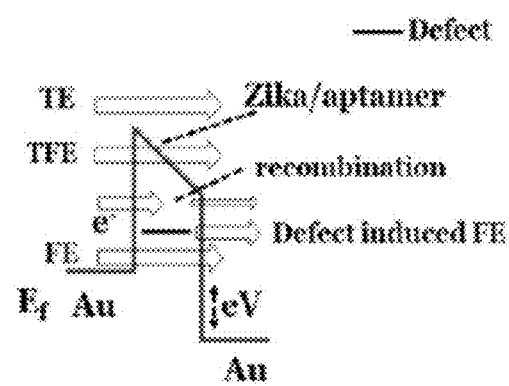

Other conduction mechanisms are also schematically shown in FIG. 10d.

In the subthreshold "leakage" current regions, different mechanisms can contribute to the current including thermal generation/recombination of charges in the barrier material, tunneling through defect energy levels (trap-assisted tunneling), field-induced charge generation, and thermionic field emission as in FIG. 10d. The current density in general is given by J=qnvd, where the vd is the drift velocity of the electrons, n is the electron density available for conduction (with a slight dependence on the junction electric field) and q is the charge. n is given by the product of total number of states D(E) and the probability of occupancy of the states given by Fermi-Dirac distribution $$f(E):n=\int_{-\infty}^{\infty}D(E)f(E)dE.$$

Hence, the current can be rewritten in the form, $$I=J\cdot A \text{ or } I=qv_d A[\int_{-\infty}^{\infty}D(E)f(E)dE],$$

where A is the cross-sectional area in the direction of the current flow. The differential conductance is obtained as $$\frac{dI}{dV} = qv_d AD(E)f(E)\frac{dE}{dV}$$

that clearly shows its relationship with the density of states.

Sensor Surface Preparation

An experiment was performed for three different types of quantum mechanical sensors. A first sensor is a conductive atomic force microscopy (c-AFM) sensor. A vertical TCS, referred to as a vertical nano-gap device, and a horizontal TCS, referred to as a horizontal nano-gap device, were also constructed. For both the c-AFM sensor and the and vertical TCS, the virus aptamer can be deposited on the gold substrate followed by depositing the virus, such as Zika, on the aptamer layer. As previously discussed, the aptamers can be specifically designed to attach to a selected protein on a virus, such as the Zika SF9 capsid protein. In this experiment, the aptamers with thiol end group as well as aptamers with amine end group were obtained. The thiolated aptamers were directly deposited on the gold-coated sample.

The Following steps were used to deposit aptamers with the amine end group. The devices were treated with 16-Mercaptodecanoic acid for 5 minutes at 60 degrees Celsius (C) and washed subsequently with ethanol. This step ensures that the thiol end of the 16-Mercaptodecanoic acid stays on the gold coated surface. After that the sensors were treated with a 1:1 solution of EDC (1-Ethyl-3-(3-dimethylaminopropyl) carbodiimide) and NHS (N-Hydroxysuccinimide) at 60 degrees C. for 2 minutes and washed with ethanol again to get rid of the excess. This step is used for direct conjugation with the amide group of the aptamer to the carboxylic acid group of the 16-Mercaptodecanoic acid which is present on the gold surface. The carbodiimide compounds (EDC and NHS) provide the cross-linking with the carboxylic group. Finally, the 2 µl of amine aptamer optioned from BasePair Biotechnologies Inc. was added having 10 µM concentration at 90 degrees C. for 2 minutes and cleaned by gently dipping in de-ionized (DI) water bath and gently blow dried with nitrogen stream. A current vs voltage (I-V) was measured using HP 4156A Semiconductor Current-Voltage Parameter Analyzer. Then 2 µl of stock solution of Zika was added to the sensor for 2 minutes at 60 degrees C. with subsequent cleaning with DI water in similar fashion as above.

Scanning Tunneling Microscopy

Figure 11:
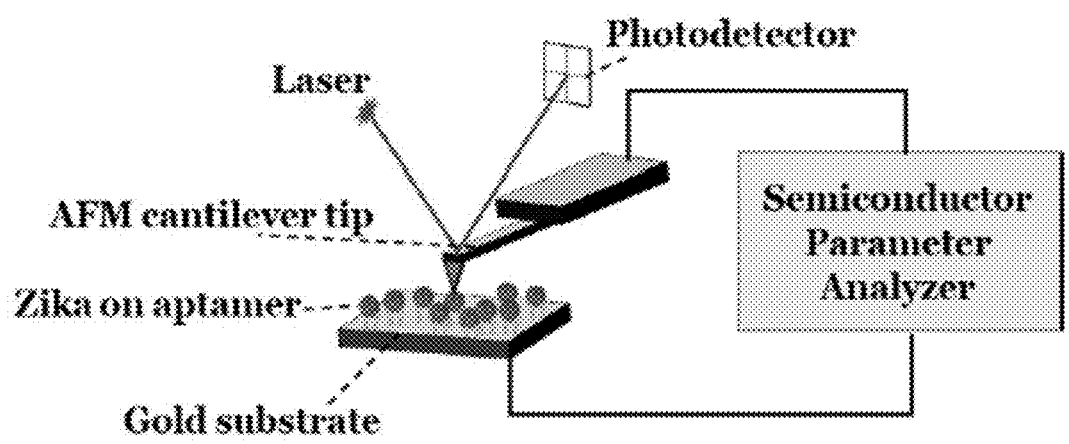
FIG. 11 is a schematic view of a conduction-atomic force microscope (AFM) for measuring a height of a virus on aptamer on a gold substrate.

FIG. 11 illustrates an example of the c-AFM system used for measuring the I-V curve of an aptamer only substrate and a Zika/aptamer on gold substrate. The c-AFM technique is sensitive to any localized changes (~10 nm length scale) on the sample surface between.

Figure 12A:
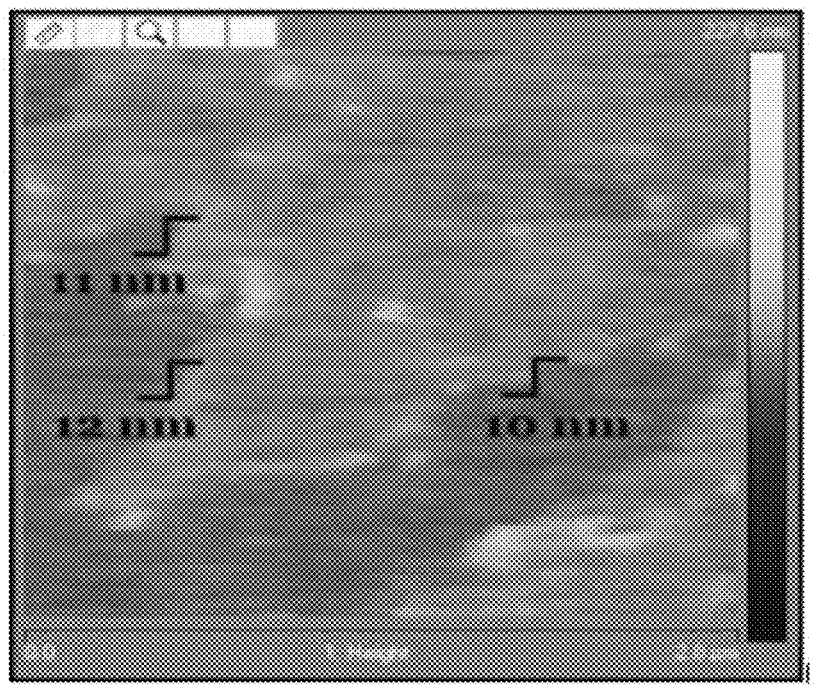
FIG. 12a is an optical image of an AFM scan performed on the aptamer on gold of FIG. 11, with an image range of 2 micrometers, and a step height of about 10 nm.
Figure 12B:
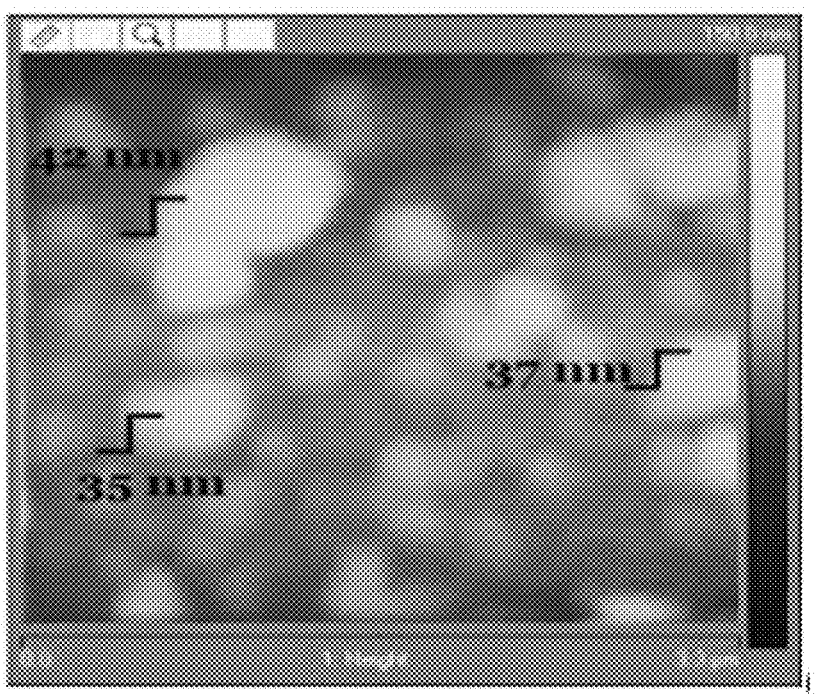
FIG. 12b is an optical image of an AFM scan performed on Zika on aptamer on gold, with an image range of 3.2 micrometers and a step height of 40 nm.

FIG. 12a shows the c-AFM scan on the aptamer on the gold coated sample. The sample was cleaned in DI water to remove the excess aptamers before the c-AFM scan. The aptamers had sulfur (thiol) functional end group to attach to the gold surface. Two different aptamers were mixed to increase Zika targeting specificity. The step-height from the bare gold surface to the top of the aptamer was approximately 9-13 nm. That step height agreed with the expected values of the two different aptamers in the mix. FIG. 12b shows c-AFM scans of the sample with a Zika/aptamer surface layer. The step heights from the aptamer surface to the top of the Zika was approximately 35-42 nm. Zika virus is a ribonucleic acid (RNA) virus. The Zika virus is a member of the Flaviviridae, similar to the Dengue virus, West Nile virus, and Japanese encephalitis virus. Zika is a 40 nm sphere with a single capsid protein with a lipid envelope, and two membrane associated proteins (M and E).

Figure 13A:
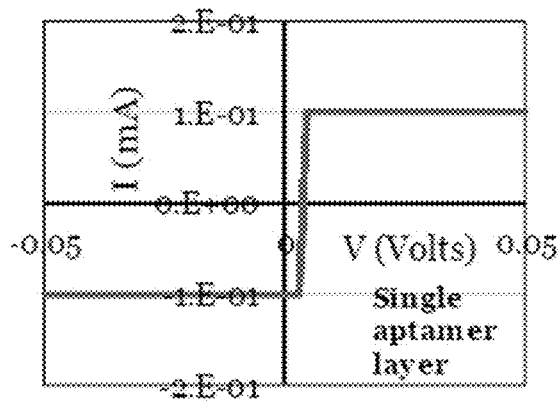
FIG. 13a is a current (I) vs voltage (V) graph of the c-AFM measurements a single layer of aptamer on the gold substrate.
Figure 13B:
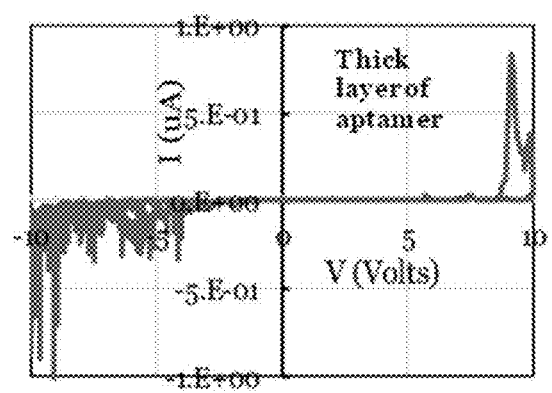
FIG. 13b is a current (I) vs voltage (V) graph of the c-AFM measurements for a thick layer of aptamer on the gold substrate.
Figure 13C:
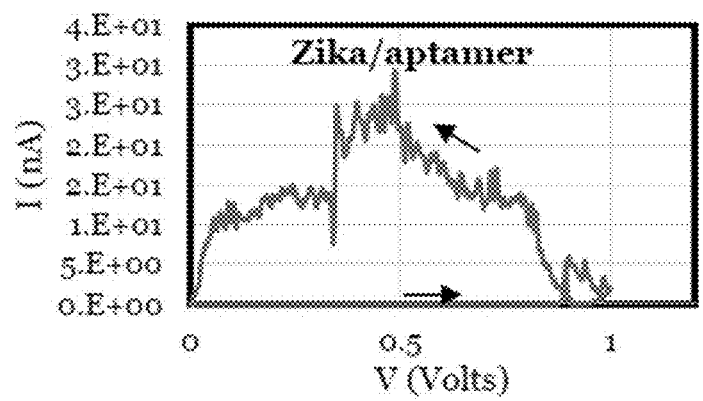
FIG. 13c is a current (I) vs voltage (V) graph for a forward bias of the c-AFM for a Zika on aptamer on the gold substrate.

The c-AFM I-V curves were then measured (FIGS. 13a-d) using samples with a single-layer (FIG. 13a) and with multiple layers (FIG. 13b) of the aptamer, and a sample with a layer of Zika on aptamer (13c, 13d). The single-layer aptamer (3-10 nm) is very conducting and carries a slightly negative residual charge as can be seen from the positive voltage (~0.005V) displaced I-V curve shown in FIG. 13a. The sample with multiple layers of aptamers (~4-5 layers) showed sub-threshold characteristics shown in FIG. 13b. The I-V curves of the Zika/aptamer sample is shown in FIG. 13c for forward bias direction and in FIG. 13d for reverse bias direction. In the reverse bias direction, the c-AFM sharp tip is negatively biased and can readily inject electrons into the sample resulting in larger currents and nearly zero turn voltage (no energy gap). I-V curves of the Zika/aptamer sample can be qualitatively explained using the band diagram schematically shown in FIGS. 14a-b.

Figure 13D:
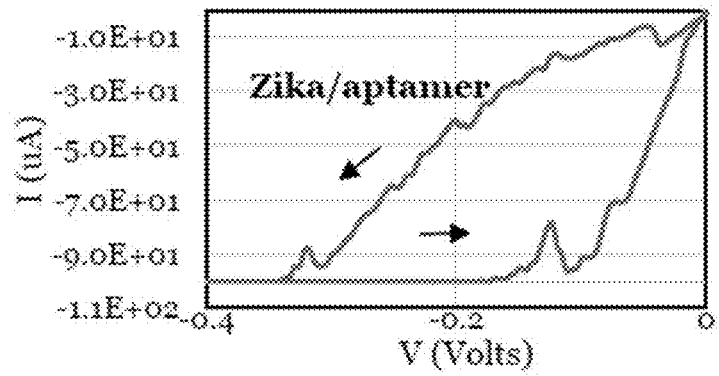
FIG. 13d is a current (I) vs voltage (V) graph for a reverse bias of the c-AFM for a Zika on aptamer on the gold substrate.
Figure 14A:
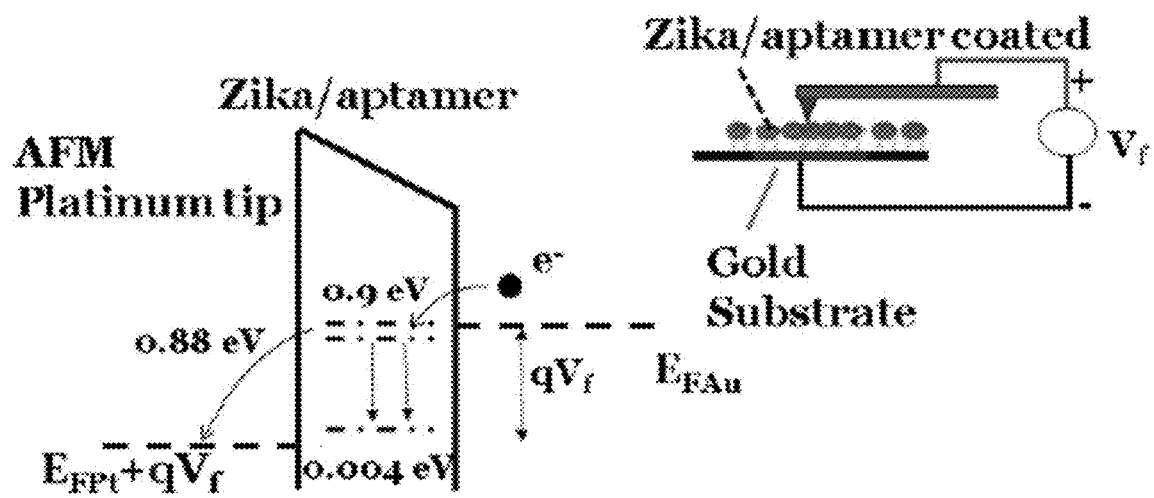
Figure 14B:
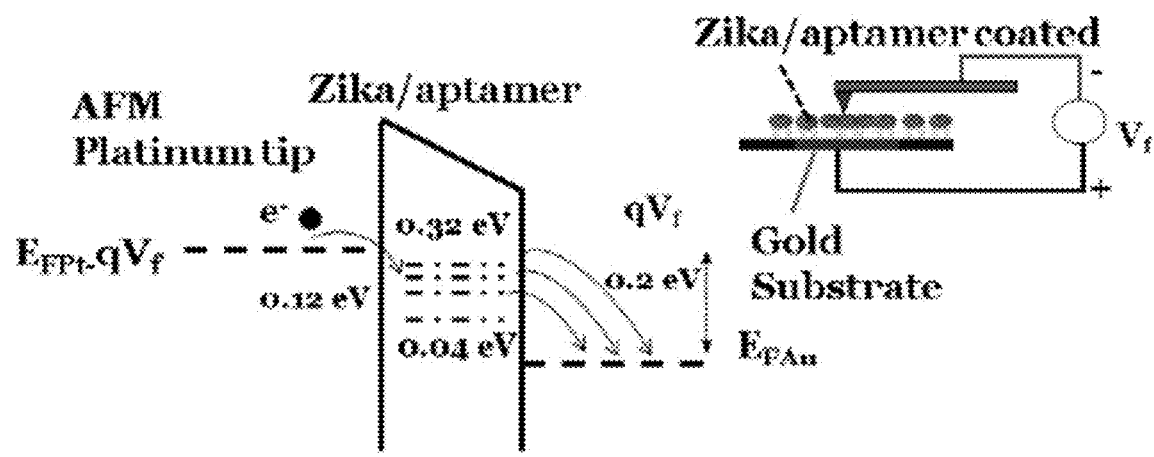

As was discussed before, in the trap-assisted tunneling, the I-V curve is directly determined by the density of the available states through which electrons can tunnel through the sample. The available states for the forward bias, shown in FIG. 14a, are at 0.88-0.9 electron volts (eV), however part of the electrons recombines and lose their energy to a trap energy level at 0.006 eV. This trap energy level at ~0.006 eV acts as an electron source when voltage activated. In the reverse bias scenario, shown in FIG. 14b, the available states are at 0.1-0.32 eV, except at 0.04 eV is a trap energy state which is voltage activated and hence there is a dip in current as seen in the I-V curve (FIG. 13d). The available states in the forward bias are at a higher energy level than that in the reverse bias condition since as stated earlier, in reverse bias the electrons are injected into the Zika/aptamer using the AFM tip. The I-V curves shown here are selected which best differentiates between the aptamer and Zika/aptamer. However, in all other cases the change in the I-V curves when Zika was present was significant compared to the bare samples and samples with the aptamers alone.

Vertical Variable Nanogap Device

The TCS device can also be configured as a vertical nanogap device. A vertical nano gap tunneling current biosensor can include a conductive sample surface oriented on a support substrate. The conductive sample surface can include molecular recognition groups attached to the surface which are configured to selectively bind with a target virus. A conductive probe tip can be oriented above the conductive sample surface and spaced therefrom to form a nano gap. A size of the nano gap can be adjustable at a nanometer scale and allows tunneling current through the conductive sample which is varied along with variations in a threshold voltage based on binding with the target virus. A parameter analyzer can also be electrically connected to the conductive probe tip and the conductive sample surface to allow detection of the varied current and the threshold voltage.

Figure 15A:
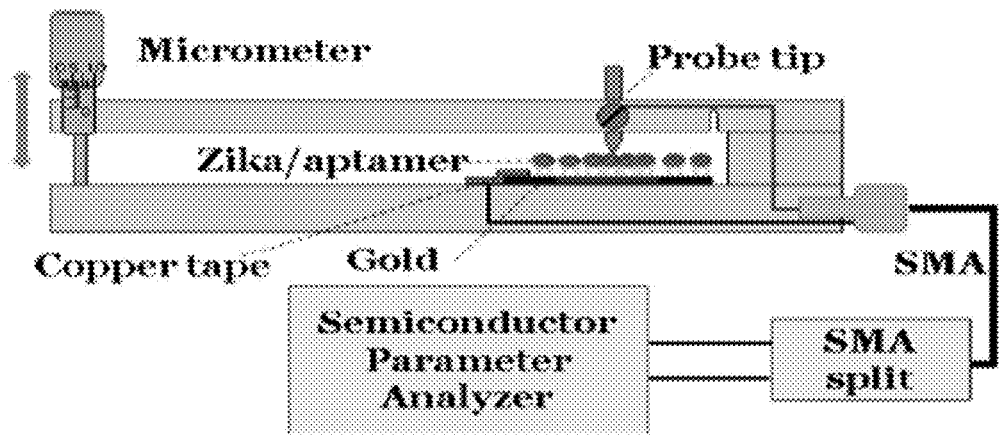
Figure 15B:
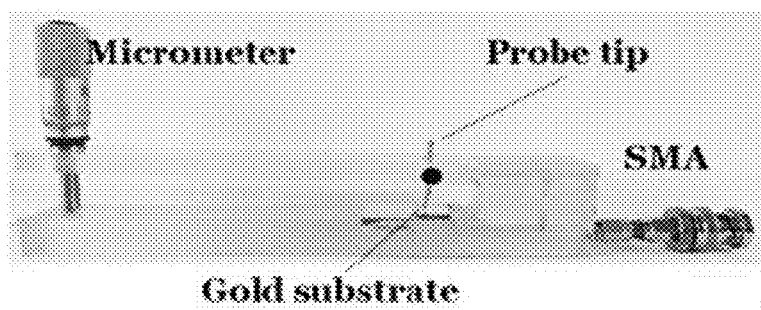
Figure 15C:
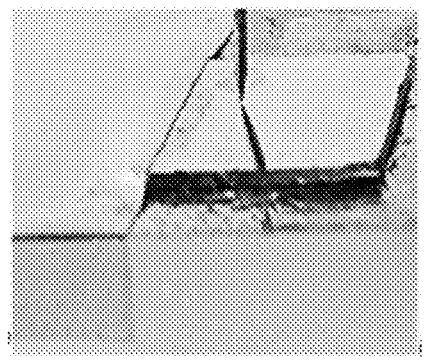

One embodiment of a TCS as a vertical device fabricated using a polycarbonate structural material, is schematically shown in FIG. 15a. The vertical device consisted of a lever situated over a base, a micrometer, a mechanism to hold a tungsten probe tip, and a region on the base to fix a conducting sample in a holder under the probe tip. An optical image of an example of a vertical device is shown in the optical image in FIG. 15b. A close up optical image of an example of a conducting sample is illustrated in FIG. 15c. The distance between the tip and the sample can be adjusted using the micrometer. In this example, the adjustment can be made with 1-to-10 lever ratio so that when the micrometer is moved by 1 µm, the tip-sample distance changed by 0.1 µm.

Figure 16A:
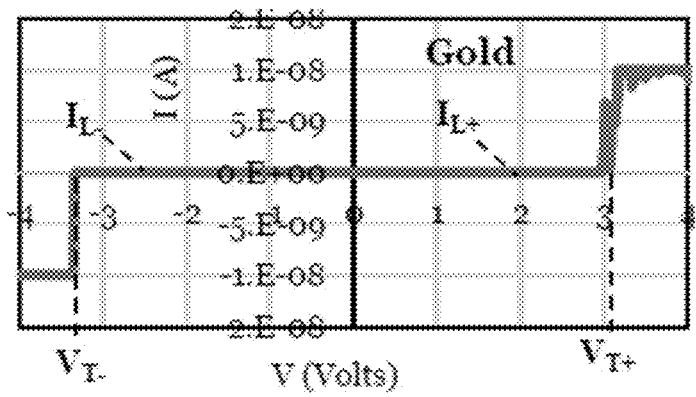
Figure 16B:
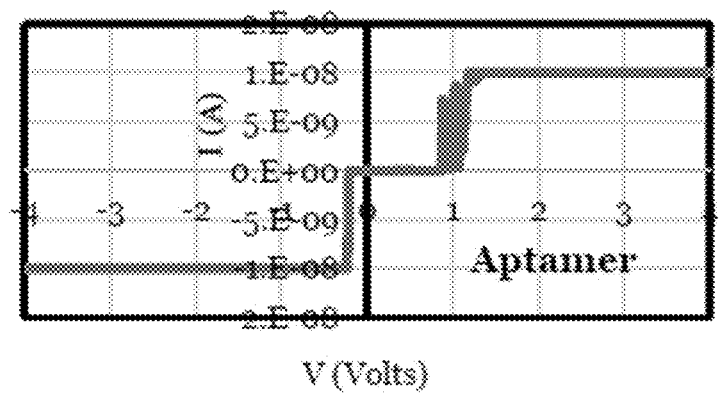
Figure 16C:
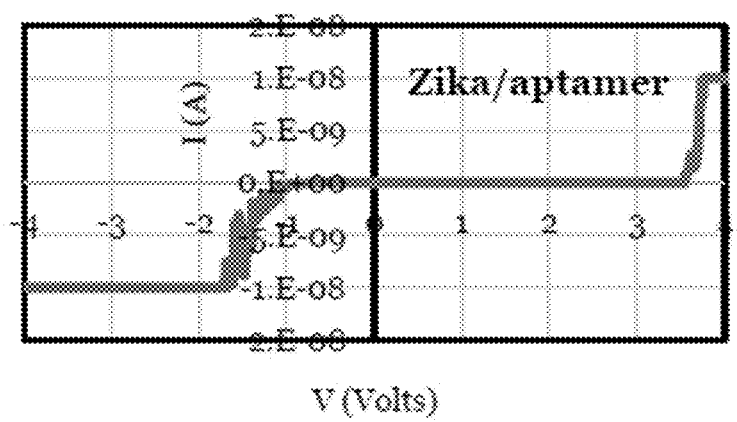

The vertical device was connected to a semiconductor parameter analyzer through the Subminiature Version A (SMA) connector for I-V measurements. In one experiment, the tungsten tip was adjusted in height until it was touching the sample. While monitoring the current at a small bias (0.1-1 V), the micrometer was adjusted to open a nano air gap between the tip and the sample. As soon as the nano-gap was formed, the current dropped from approximately micro Amps (µA) to $10^{-9}$-$10^{-8}$ Amps (i.e. nano Amps (nA). FIGS. 16a-c show the I-V for different samples. The turn-on voltage depends on the material of the probe tip and the sample.

FIG. 16a shows the vertical TCS I-V curve with a bare gold sample. The threshold voltages of approximately +/−3 V are associated with the tungsten oxide energy band gap (~2.6-3.3 eV depending on the water content) on the tungsten tip. FIG. 16b shows the I-V curve of a sample with Zika aptamer on the gold sample. In this case, the wide band gap that is typically present due to tungsten oxide on a tungsten probe tip seems to be absent. The threshold voltages are much smaller than the bare sample case and the asymmetry between $V_T+$ (~1 V) and $V_T-$ (~0.2 V) is much larger than before.

Figure 17A:
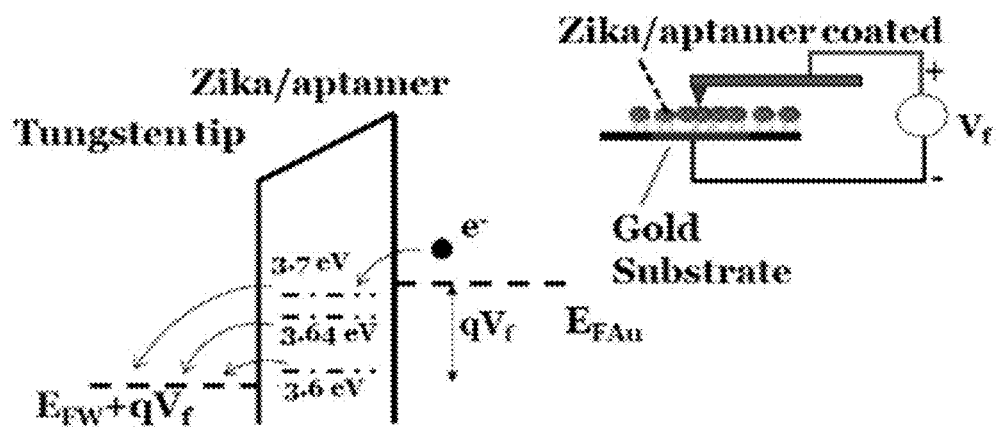
Figure 17B:
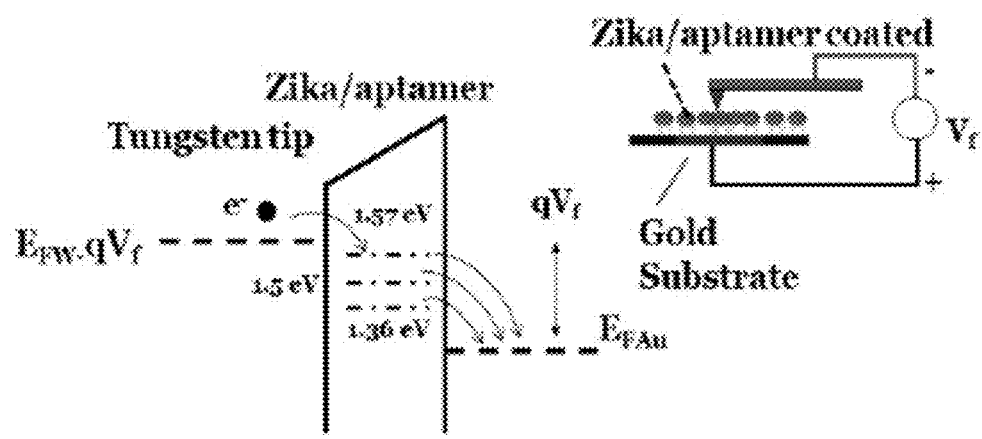

The I-V curve of the Zika/aptamer sample is shown in FIG. 16c. The $V_T-$ in this case is very small while the $V_T+$ corresponds to the tungsten oxide energy band gap. The density of states in the forward bias direction seems to be located at 3.6-3.7 eV and in the reverse direction at 1.36-1.57 eV as schematically shown in FIGS. 17a-b, which illustrate the band diagram of Zika on aptamer on a gold sample in the forward (FIG. 17a) and reverse (FIG. 17b) directions.

Lateral Nanogap Device

The vertical device is configured such that the sample is configured to be placed inside the device and the micrometer is to be adjusted to form the nano air gap. The sample can be quite delicate. In addition, the probe tip can be extremely delicate. If the tip comes into contact with another surface, it can easily be damaged. Thus, the need to place the sample in the device and adjust the tip height can be problematic for a field deployable TCS.

Figure 18A:
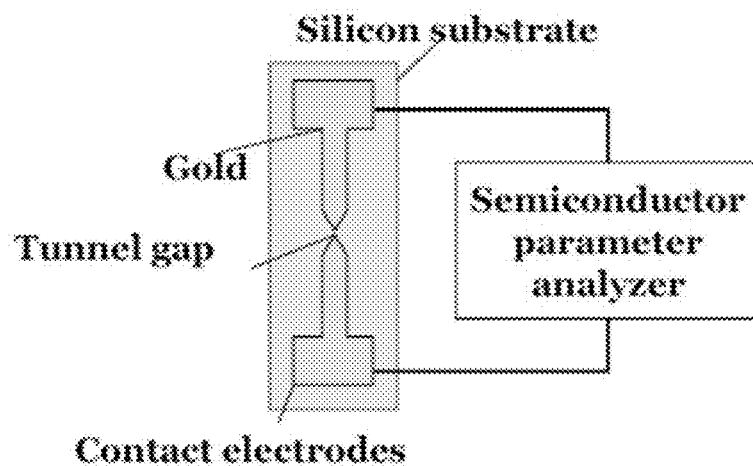

A lateral nanogap device structure is schematically shown in FIG. 18a that eliminates the need for a user to move the sample and adjust the probe height. In addition, the lateral nanogap device can also be micro fabricated.

In one example, a lateral nano-gap quantum tunneling current biosensor can be formed on a semiconductor substrate. As previously discussed, the semiconductor substrate can be comprised of a selected semiconductor, such as silicon, gallium arsenide, germanium, boron, indium, carbon nanotubes, or another desired semiconductor. A low stress bridge material can be deposited on the semiconductor substrate. The low stress bridge material can be selected to minimize mismatch between the atomic lattice of the semiconductor and the bridge material. The low stress bridge material can generally have 0-50 MPa residual stress. These criteria can be achieved by considering choice of materials, thicknesses, and adjacent adhesion and support layers. Non-limiting examples of suitable bridge materials can include silicon dioxide, polysilicon, aluminum nitride, etc. In one example, the bridge material can be formed of silicon nitride.

An adhesion layer can be deposited on the low stress bridge material. The adhesion layer can be formed of one of more of chromium, titanium, nickel, and combinations thereof. Optionally, the adhesion layer can be functionalized to bond with the aptamer, or other molecular recognition group. A first electrode can be deposited on the adhesion layer and configured to be connected to a parameter analyzer. A second electrode deposited on the adhesion layer and configured to be connected to the parameter analyzer. The electrodes can be formed using formed using one or more conductors comprising silver, gold, copper, platinum, aluminum, zinc, cobalt, nickel, tungsten, or ruthenium, or combinations thereof.

A nano-gap can be located between the first electrode and the second electrode, the nano-gap forming an air gap between the first electrode and the second electrode with a gap width sufficient to enable a tunneling current between the first electrode and the second electrode when a voltage differential is provided between the first electrode and the second electrode. An molecular recognition group can be located in the airgap. As previously discussed, the molecular recognition group is configured to bind to a selected virus. The parameter analyzer can be configured to detect a change in the quantum tunneling current through airgap over a range in voltage. The change in the tunneling current can be used to identify when the selected virus is bound to the molecular recognition group.

In one example, the adhesion layer can be functionalized to bond with the molecular recognition group. Alternatively, a separate material, such as gold can be deposited on the adhesion layer. In FIG. 8a, an adhesion layer can be deposited on the $Si_3N_4$. The gold can then be deposited on the adhesion layer. The separate material, such as the gold, can be functionalized to bond with the molecular recognition group.

Figure 18B:
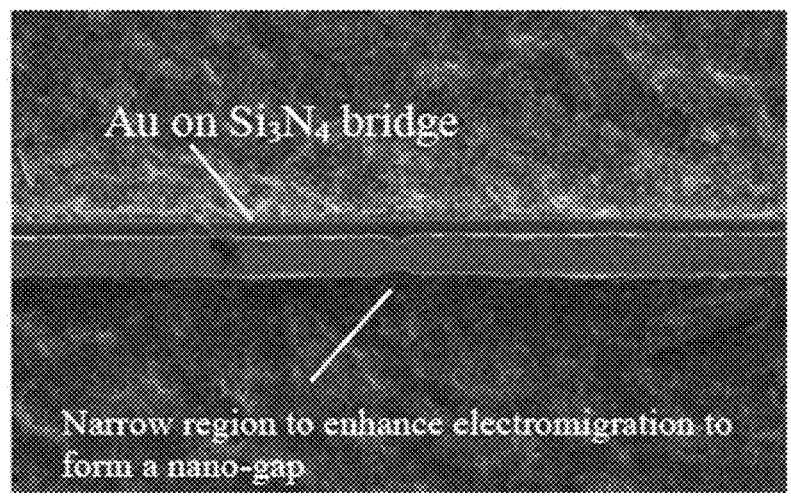

In another example, a silicon nitride bridge can be formed on a silicon substrate, as illustrated in the optical image of FIG. 18b. In this example, the silicon nitride bridge is 5 µm-wide and 500 µm long. The bridge was released using XeF2. A gold interconnect can be deposited on the bridge as a 1 µm wide, 100 nm thick gold interconnect with a 20 nm chromium adhesion layer that is deposited and defined using optical photolithography on a 100 nm thick plasma enhanced chemical vapor (PECVD) deposited silicon-rich (low stress) Si3N4 bridge on the silicon substrate.

Figure 18C:
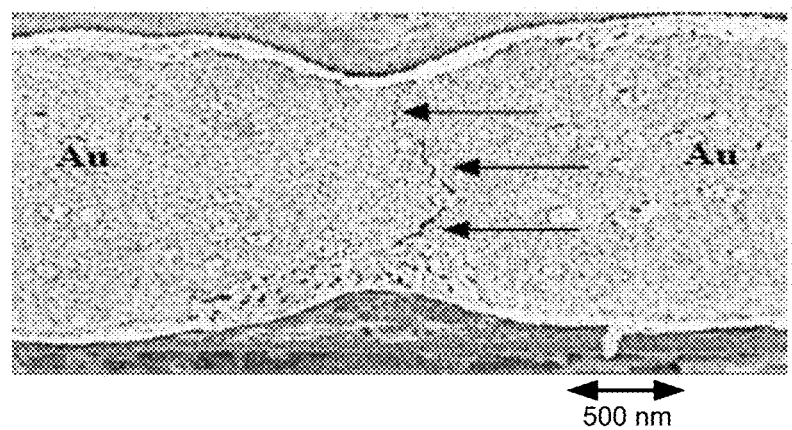
Figure 19:
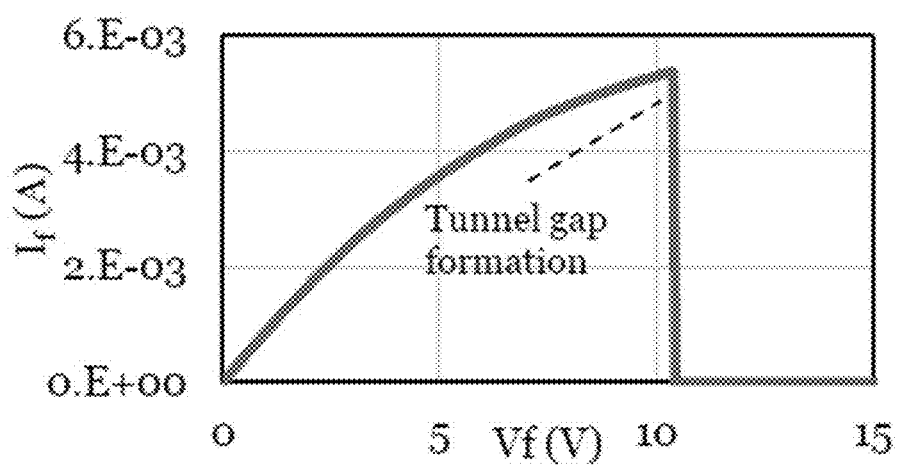

Forming an air gap of a few nanometers wide can be challenging, even with modern manufacturing techniques. FIG. 18b provides an example for creating a nano air gap that can be formed without the need for complex manufacturing processes. In this example, a narrow region is formed in the gold that is deposited on the silicon nitride bridge. The narrow region can enhance electro-migration of the gold particles. A current was then repeatedly passed through the gold interconnect line to cause electro-migration of gold atoms in the region with reduced linewidth shown in FIG. 18b. FIG. 19 shows the I-V curve of the measurement associated with the formation of the nanogap. The voltage along the gold metallization line can be ramped from a first voltage to a second voltage a plurality of times. This repeated ramping can be performed until the air gap is formed that reduces current to a selected current level. For example, voltage can be ramped from 0 V to a relatively high voltage, such as 40 volts a number of times. Each time the voltage is ramped, gold atoms migrate in a selected direction across the narrow gap. In this example, the voltage was ramped to 40 volts five times. When the voltage was ramped a sixth time, FIG. 19 shows that the current dropped precipitously at 10.5 V in the 6th run. The significant drop in current indicates the opening of a gap in the gold metallization line. The nano-gap is shown in the optical image of FIG. 18*c*. The arrows show the nano gap. The scale bar in FIG. 18*c* is approximately 500 nm. The width of the air gap can be selected based on a size of the selected virus.

The electromigration in the gold metallization layer may be responsible for opening the air gap seen in FIG. 18*c*. The gap formation is also facilitated by the silicon nitride bridge that flexes due to thermal expansion when the voltage is ramped along the gold metallization line. Additionally, the nitride layer thermally isolates the heated gold region that increases its temperature and speeds up the electromigration process that has an activation energy of 0.8 eV in gold. The time-to-gap opening exponentially depends on temperature. Using voltage sweeps on the conductive layer can enable the creation of a nano-gap without the need for complex manufacturing processes.

Figure 20A:
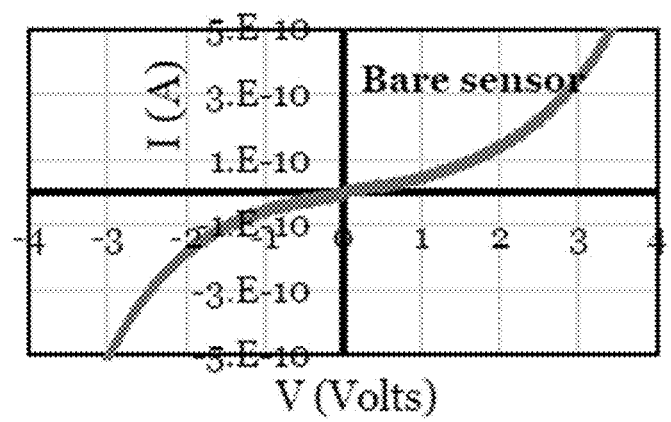

The I-V characteristics of the tunnel junction after the gap formation is shown in FIG. 20*a*. The device I-V curves through the aptamer and Zika/aptamer complexes are shown in FIGS. 20*b* and 20*c*, respectively.

Figure 20B:
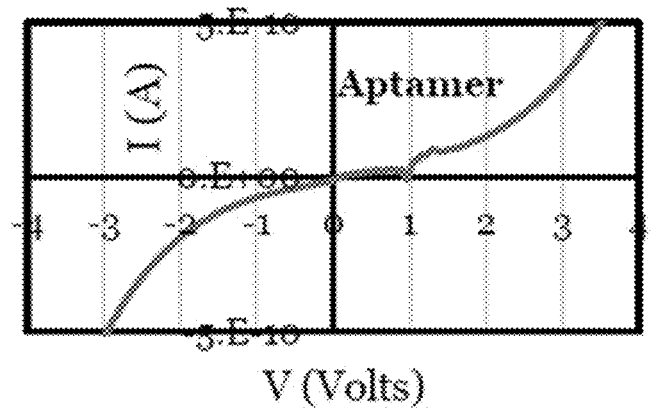
Figure 20C:
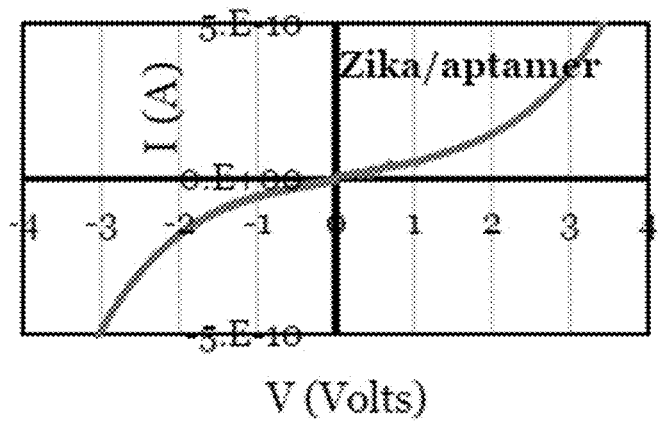
Figure 21A:
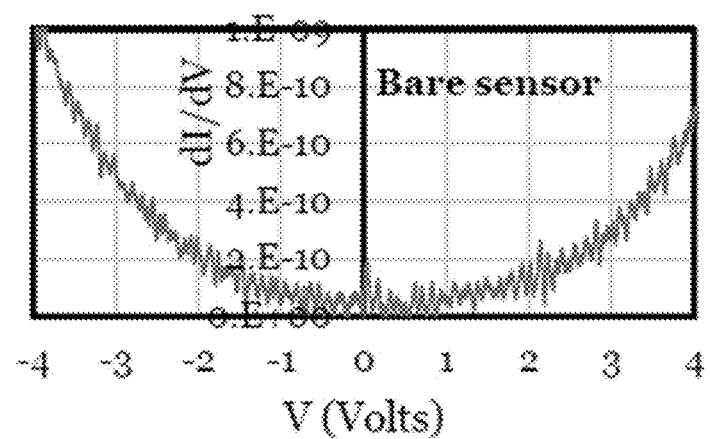
Figure 21B:
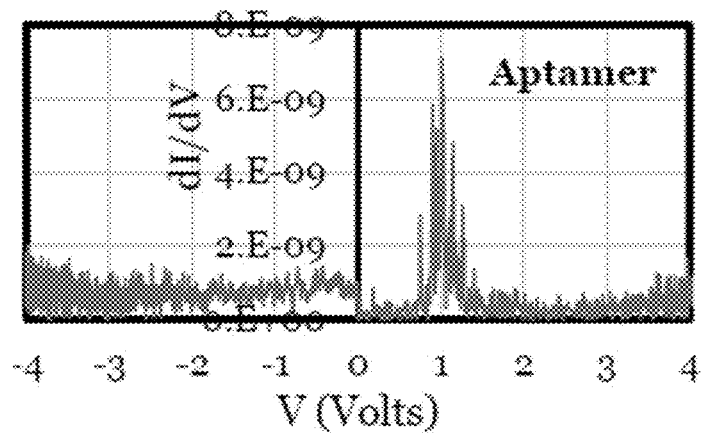
Figure 21C:
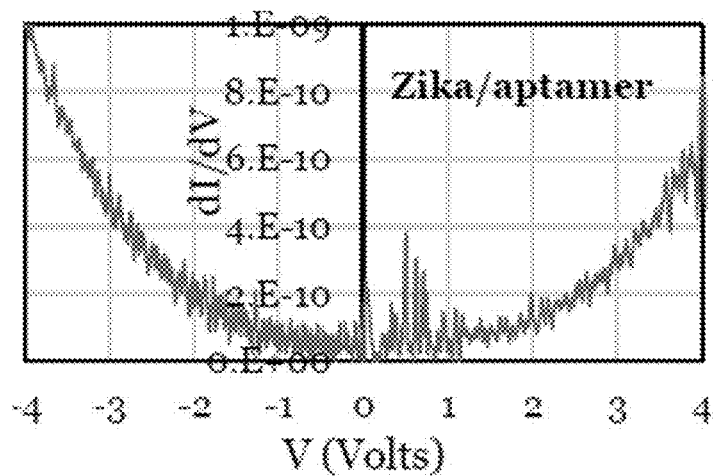

The differential conductance (dI/dV) plots constructed using the I-V curves in FIGS. 20*a-c*, are shown in FIGS. 21*a-c*. The bare sample dI/dV does not have a threshold voltage indicating a zero energy band gap of the TCS that is expected since the electrodes on both sides of the tunnel junction are gold. Both the aptamer and the Zika/aptamer samples had non-zero dI/dV respectively at +1 V and +0.5 V.

The tunneling current sensor has a very small minimum detectable signal approaching the detection of a single atom at room temperature and can easily detect a single virus reliably.

However, to enable a TCS, such as the lateral nano gap device, to reliably identify a virus, such as the Zika virus or the Covid-19 virus is quite challenging. The TCS output characteristics are composed of two threshold voltages (VT+ and VT−) and two sub-threshold currents (IL+ and IL−) as shown in FIG. 16*a*. The threshold voltage is related to an effective energy band gap in the insulating/semiconducting virus or an oxide layer in the gap. The leakage current is related to the defect energy states inside the energy gap. The presence of moisture and other contaminants (sodium chloride, carbon dioxide, etc.) along with the nano-gap size variation, instability of the TCS metal electrodes, variations and defects in the virus surface proteins and the presence of residual DNA/RNA and other macromolecules on the virus, can drastically change the TCS output.

The TCS's specificity comes from the specificity of the aptamers that are positioned in the gap, as illustrated in the example TCS of FIG. 8*a*. The aptamers that molecularly target the pathogens or, in this example, viruses such as Zika or Covid-19 or another coronavirus. The pH of the solution containing the analyte, as well as the condition of the surface protein of the virus and operation temperature as well as aptamer-substrate binding strength and aptamer-virus binding strength all affect the sensor performance including selectivity and sensitivity. One strategy to increase the sensor specificity is to use many different aptamers that bind to different surface proteins of the virus.

In one example, a plurality of lateral nano-gap tunneling current biosensors can each be bonded to the silicon substrate, with each biosensor including a first electrode and a second electrode that are configured to be coupled to the parameter analyzer. The parameter analyzer can be configured to detect a change in the tunneling current for each of the plurality of lateral nano-gap quantum tunneling current biosensors. The change in the quantum tunneling current of two or more of the plurality of lateral nano-gap tunneling current biosensors can be used to identify when the selected virus is bound to the molecular recognition group.

In one embodiment, the uncertainty associated with the TCS's output because of its nearly exponential dependence on the above parameters, can be compensated for by using the output of a plurality of TCS devices, such as the lateral nano-gap device illustrated in FIGS. 18*a-c* or the TCS device illustrated in FIG. 8*a*. A "pattern" can be obtained from the plurality of TCS devices for a given sensing task. One can then use machine learning algorithms to "classify" the output of TCS sensors for reliable and label free detection of a virus, such as a desired coronavirus. This technique can detect a single virus without requiring molecular labels. It can also be adopted to fabricate reliable and field-deployable virus sensors.

Figure 8B:
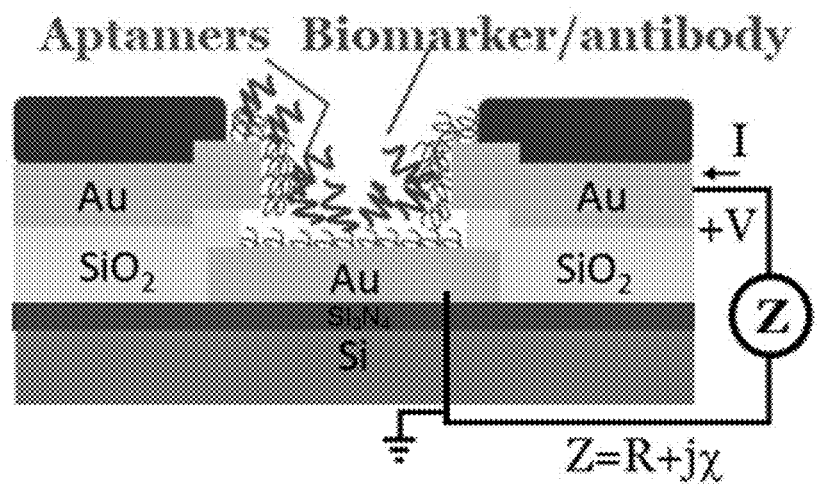
FIG. 8b is a schematic view of a tunneling current sensor with aptamers attached to a gold surface in a nano air-gap sized for a biomarker or antibody.
Figure 8C:
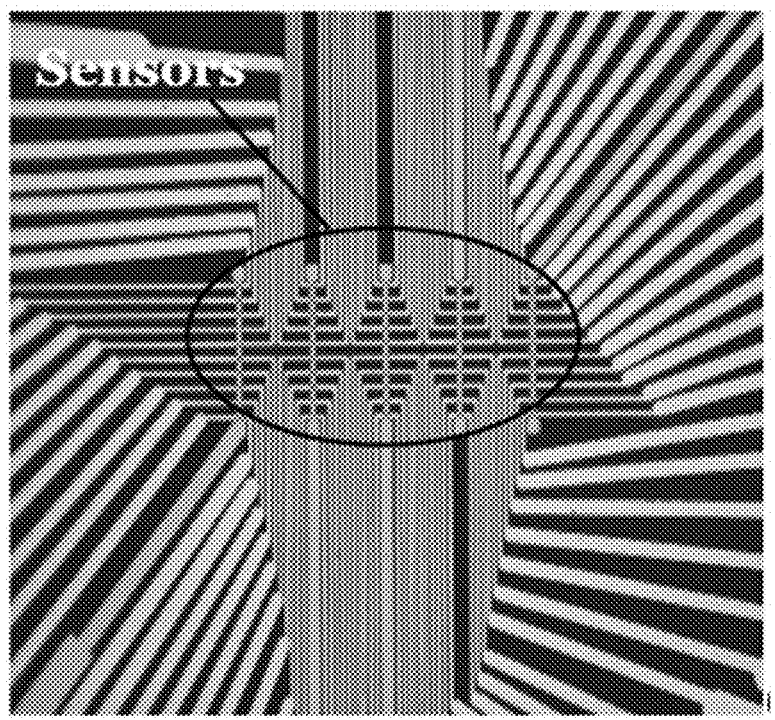
FIG. 8c is a schematic view of an array of TCS on a semiconductor substrate.
Figure 9C:
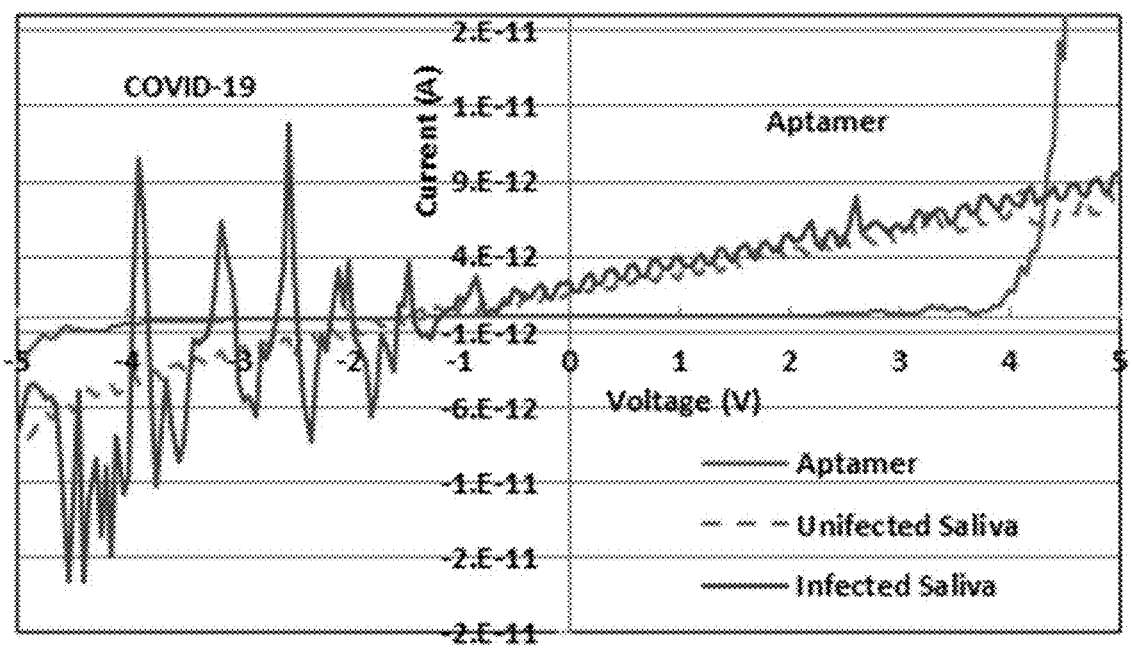
FIG. 9c is a graph of current versus voltage for a sensor of FIG. 8c.
Figure 9D:
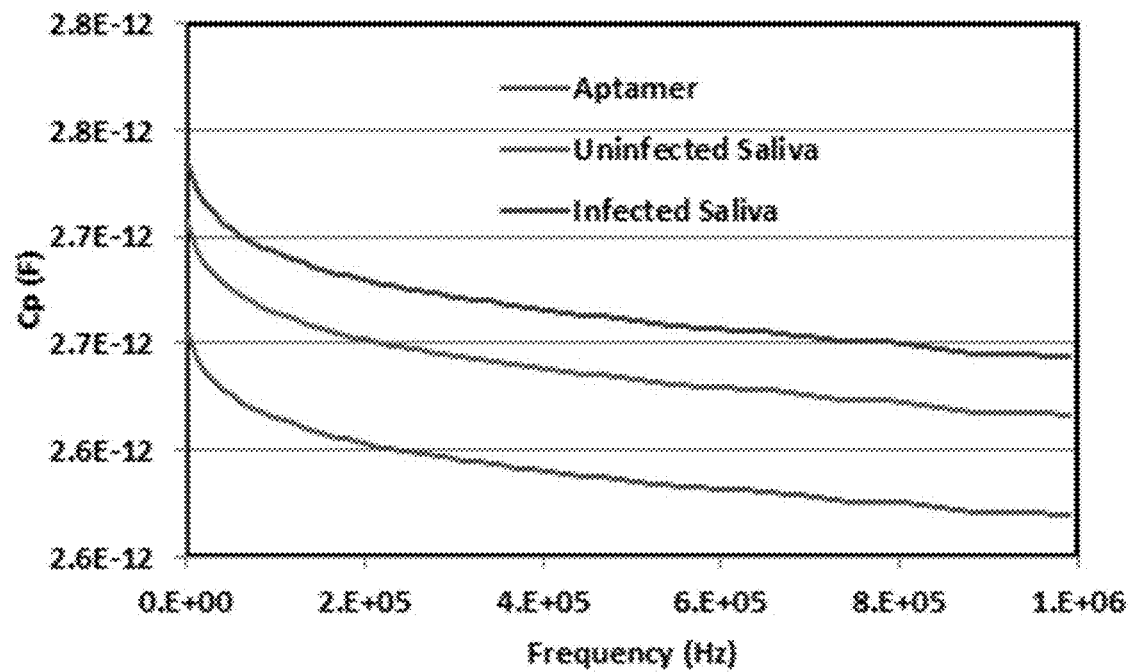
FIGS. 9d and 9e are graphs showing parallel capacitance and resistance of the device of FIG. 8c.
Figure 9E:
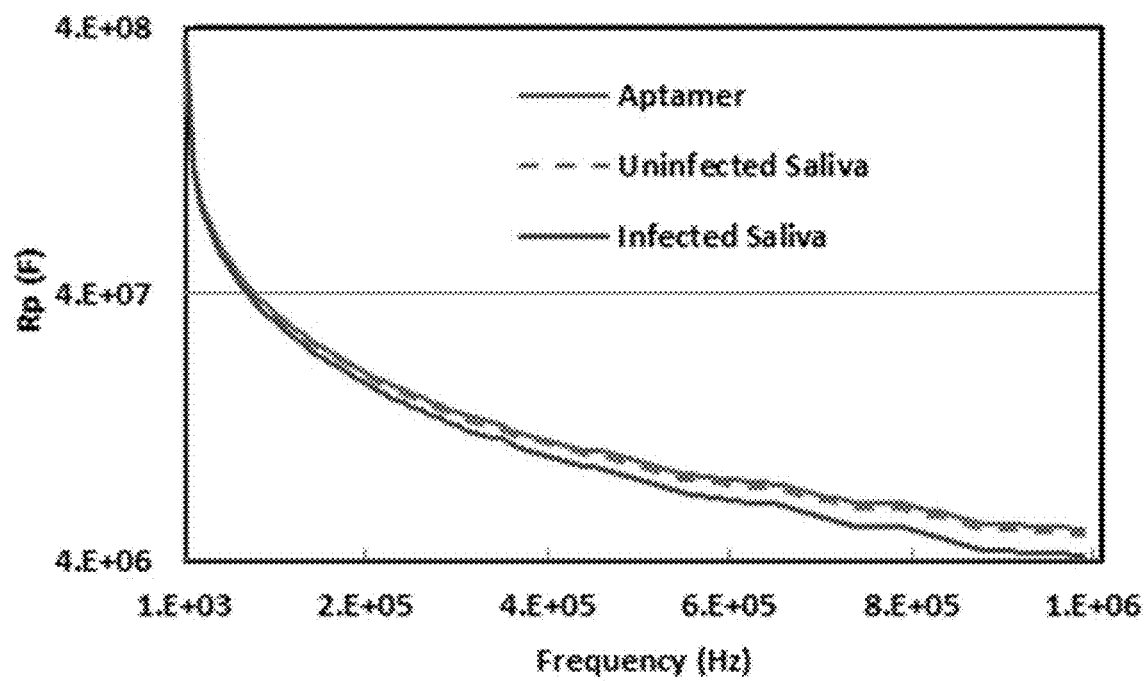
Figure 9F:
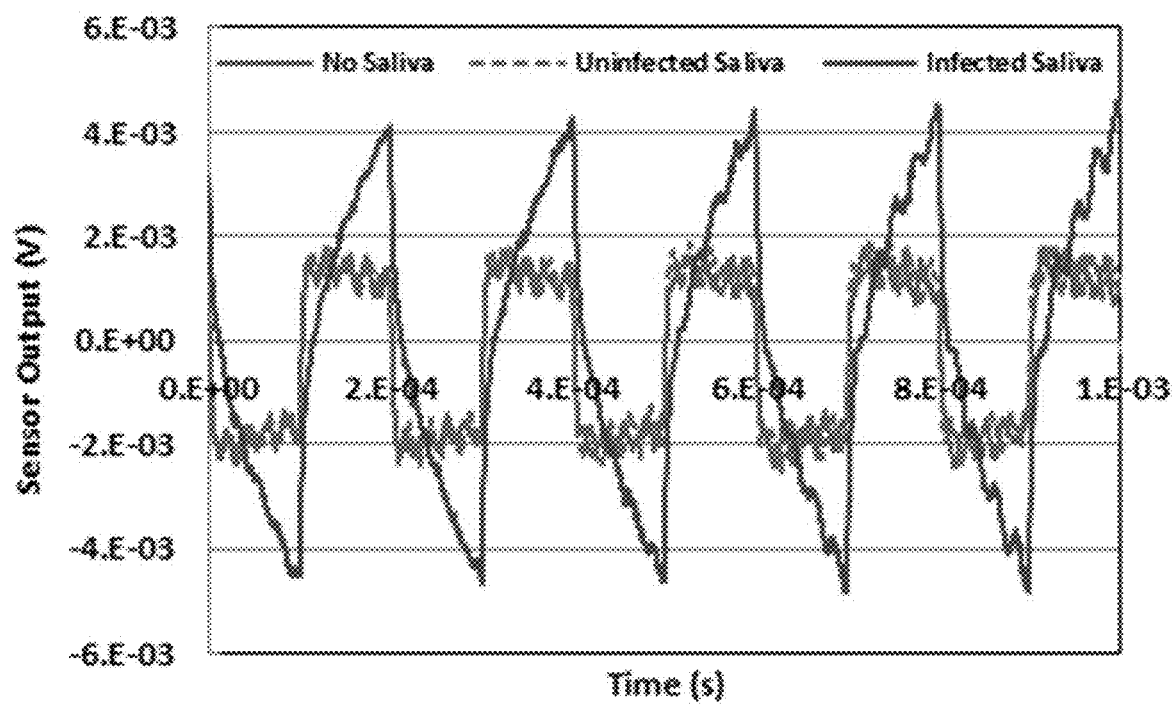
FIG. 9f is a graph of a response output waveform with a square wave excitation of the device of FIG. 8c.

FIG. 8*a-b* shows two quantum mechanical tunneling current sensors that can be readily fabricated using standard cleanroom microfabrication techniques. The top-bottom gap distance that is determined by the biomolecule/virus size is precisely fabricated using the thickness of the sputtered oxide layer. The control of thickness can be a single atomic layer around 3.5 angstrom resolution. The lateral dimensions can be defined by photolithography techniques to be lower than 1 µm. In these devices gold on chromium can be used for the top and bottom electrodes. FIG. 9*c* shows the sensor output to uninfected and infected saliva. FIG. 9*c* shows the current versus voltage characteristics of one of the sensors shown in the array of FIG. 8*c*. The sensor had 100 nm vertical gap and 1 µm wide top electrode. The quantum mechanical tunneling current is clearly detecting the aptamer and the virus as a marked change in the current at voltage above about 2V, and below about −2V. FIGS. 9*d* and 9*e* show the parallel capacitance and resistance of the same device as a function of frequency. The larger capacitance at lower frequencies is observed for samples with virus. A larger capacitance associated with the virus also results in a distinct sensor output waveform (0-3.3 V, 5 kHz, 50-50 cycles) in response to a square wave excitation shown as shown in FIG. 9*f* These sensors have close to 100% accuracy.

TCS devices can be used in the field to provide fast and accurate detection of viruses. The ability to rapidly test people and obtain nearly instant results can significantly reduce outbreaks of a virus. They can even be used to stop outbreaks from happening. TCS devices can be useful in developed areas of the world, where high tech manufacturing exists along with highly skilled workers capable of manufacturing the TCS and using them to perform tests.

Significant characteristics of quantum mechanical tunneling current sensors is that they provide molecular recognition through three different mechanism of their aptamers, gap size (designed to match the size of the virus), and unique I-V signatures associated with different viruses. As a result, these sensors are fast and can be readily measured using square wave excitation.

Paper Based Biosensor

In another embodiment, lower cost sensors would be more useful in underdeveloped portions of the world. When a pandemic hits, first world countries can become more insular. Loans and technical support for third world countries can dry up fast. Accordingly, virus detection sensors that can be manufactured and used in third world countries can be very beneficial. Since underdeveloped countries often have limited medical capabilities, it can be even more important to detect those that are sick with a novel virus and quarantine them. The ability to rapidly and inexpensively detect those that are sick, and trace and test those that they may have come in contact with, can save millions of lives in a highly contagious outbreak of a novel coronavirus.

Sensors built with paper as a substrate have short response time, are low-cost and they are flexible. Moreover, they are biodegradable and suitable for mass deployment in resource limited areas and can be easily used by unskilled operators. Paper is also great medium for immobilizing and trapping and in some cases binding with biomolecules. Paper's porous structure with large connected pores composed of cellulose fibers allows the paper to transport liquid by means of capillary forces that result in short response time. The porous structure of paper also allows any nano and micro particles to remain immobilized in the paper structure. Paper can be functionalized with certain materials such as nitrocellulose paper used for immobilizing nucleic acids for selective sensing like. Paper-based potentiometric sensors are reported for detecting many ions and proteins. Potentiometric paper-based sensors utilize gradients of ion distributions that generate open circuit voltages (Voc) that are measured to transduce analytes.

There are many types of virus sensors and detection methods reported in the literature. These include serum analysis using the antibody detection assays and detection of viral RNA using molecular-based techniques like conventional polymerase chain reaction (PCR). Real-time reverse transcription polymerase chain reaction (RT-PCR) Zika are also reported. These techniques involve using viral antibody or DNA/RNA extraction followed by labelled detection using fluorescent probes. They provide high sensitivity and specificity but require specialized equipment and expensive procedures and are time consuming. The paper-based sensors are fast, inexpensive and can be used in regions with limited resources. We show that a simple LCD can be used to measure the sensor output with the power generated with the sensor itself. The paper sensor reported here can be modified by replacing its aptamer with aptamers (or other molecular recognition groups) for other viruses, such as COVID-19, pathogens and even bacteria.

Figure 23A:
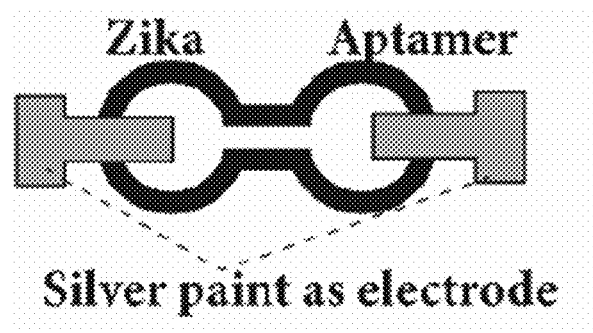

In accordance with an embodiment, it has been found that a potentiometric paper sensor can reliably detect a whole virus using standard printer papers functionalized with molecular recognition groups. In selected sensors, when a virus, such as Zika, was added to one side of the paper, it resulted in a concentration gradient with the associated electrochemical potential difference. Electrical contacts to the paper sensor can be made with Graphene, conducting glues, and epoxies or silver paint. A proof-of-concept device was developed (FIG. 23a) that can be printed with silver paint contacts and show that the paper-based virus detection sensor can be connected to an LCD for electronic readout.

Theoretical Background for Paper Sensors

Figure 22A:
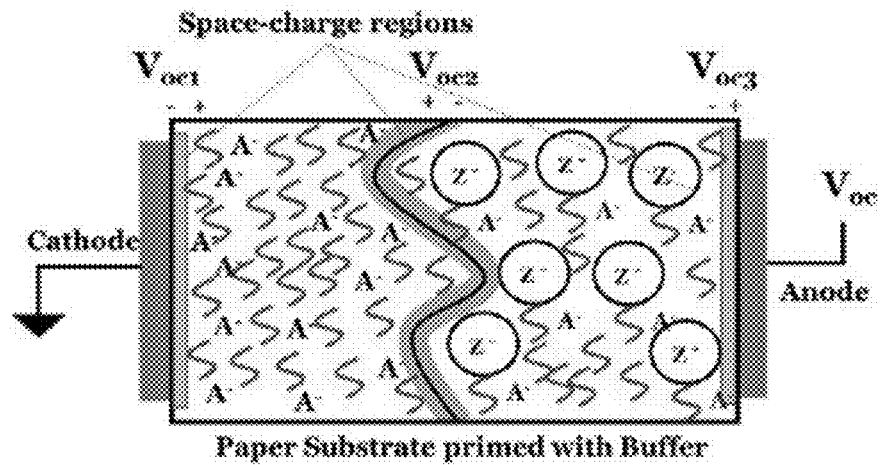

The charge distribution and ionic transport of different charged species in the paper device and the resulting open circuit voltage, can be explained using phase boundary model formed by two different ionic species (aptamer in the background and Zika added on the anode side). The total electrochemical potential difference (Voc) (FIG. 22a) is the sum of the phase boundary potentials between the aptamer-electrode (Voc1), the liquid junction potential between the Zika-62 aptamer-aptamer (Voc2) and between the Zika-aptamer-electrode (Voc3): Voc=Voc1+Voc2+Voc3. FIG. 22a shows the schematic of the phase boundary between electrodes and the paper and liquid junction potential at the center. The phase boundary potential between the aptamer-electrode (Voc1) and Zika/aptamer-electrode (Voc3) are obtained from the Nernst equation:

$$[Aptamer-] \rightleftharpoons [Aptamer] + e^- \text{ and } [Zika-] \rightleftharpoons [Zika] + e^- \quad (1)$$

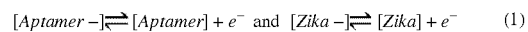

$$V_{oc1} = -V_0 + \frac{RT}{Z_1 F} \ln \frac{1}{[Aptamer^-]}, \text{ and} \quad (2)$$

$$V_{oc3} = V_0 - \frac{RT}{Z_3 F} \ln \frac{1}{[Zika^-]},$$

where, $V_0$ is the standard potential, R is the gas constant, T is temperature, F is the Faraday 72 degree constant (Coulombs/mol), $Z_1=1$ is the valence of the aptamer and $Z_3=1$ is the valence of the Zika. Zika is a complex extended pathogen with surface proteins, DNA, RNA, etc. and has many oxidation/reduction potentials corresponding to more than one charge transfer indicated in Equation 1. However, under the small voltages and chemically "mild" conditions of the paper sensors, it is reasonable to assume that single valency indicated in Equation 1 is reasonable.

The liquid junction potential between (Zika-aptamer) and aptamer in the middle of the device (FIG. 22a) can be written as:

$$V_{oc2} = -\Sigma_i \frac{RT}{FZ_i} \int_1^m t_i d(\ln C_i) \quad (3)$$

where, Zi is the valence of the particular sample species (in our case Z's for aptamers and the Zika are equal to 1), $C_i$ denotes the activity of the ions/sample species and $t_i$ is the transference number and signifies the fractional conductance of the ith ion/sample species. The transference number defined by $$t_i = \frac{|z_i| u_i M_i}{\Sigma_j |z_j| u_j M_j},$$

where u is the mobility of the ith ion and $M_j$ is the molar concentration, with j ranging over all the ions. We note that there are 3 space charge regions that form (FIG. 22a) between the anode/cathode and the paper and at the boundary of the Zika region in the middle.

Figure 22B:
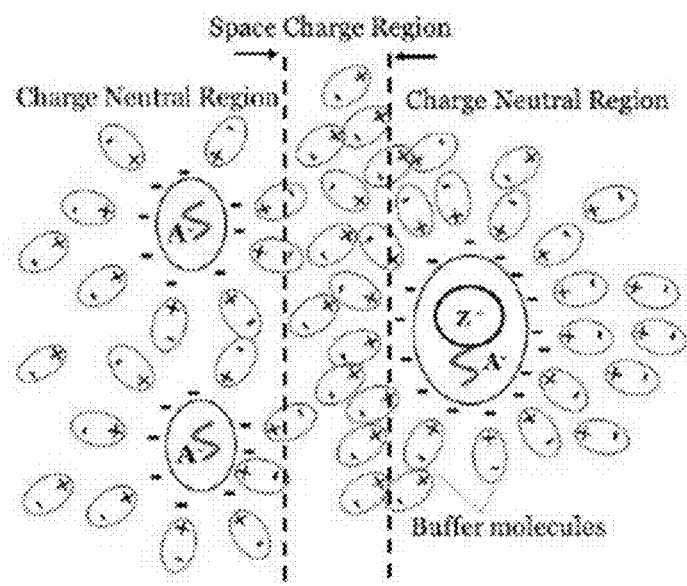
Figure 22C:
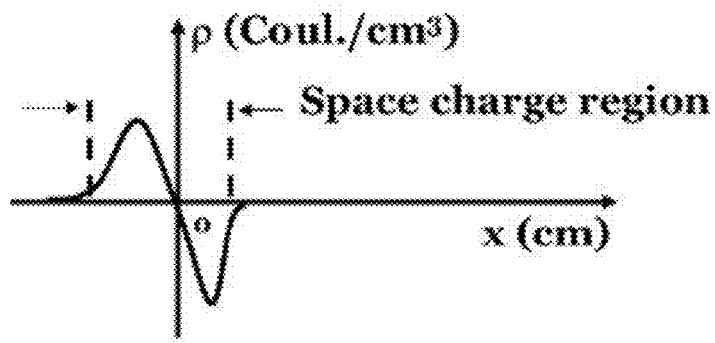
Figure 22D:
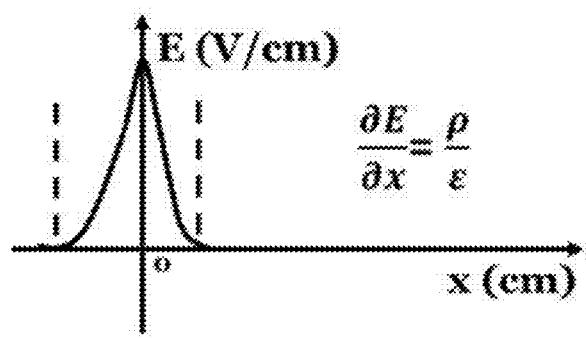
Figure 22E:
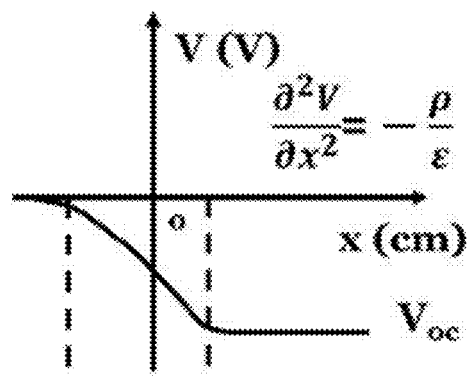

In selected experiments, the paper was primed with the buffer solution and aptamers. It is assumed that the anode-paper and cathode-paper Nernst potentials (Voc1 and Voc3 in FIG. 22a) are approximately equal and are determined by the electrochemical potential differences between these electrodes and the primed paper. Thus, Voc1=Voc3 and the total Voc between the cathode and the anode is approximately equal to Voc2 (FIG. 22a). The space-charge region at the Zika boundary (FIGS. 22a and 22b) is composed of charges that are induced by the Zika-aptamer-buffer on one side of this junction and aptamer-buffer on the other side (FIG. 22b). The aptamers and Zika viruses become immobilized in the pores of the paper. According to experiments the aptamer and Zika had negative residual charges. Each of these analytes are charge neutral but when they are added together, because of their different polarizability, they exhibit different residual charges. In the case of Zika+aptamer, there is an additional charge re-distribution because of bonding. The bonding process does not happen instantly and proceeds as a function of time at room temperature. In our experiments, the Zika-aptamer complex provided higher Voc change than Zika alone. The selectivity of the sensor to detect Zika is primarily due to its preferential binding with the aptamer. When the Zika is added to the anode region, Voc became negative suggesting that the space charge region has a charge, electric field and potential distributions schematically shown in FIGS. 22c, 22d and 22e.

Materials and Methods

Figure 23B:
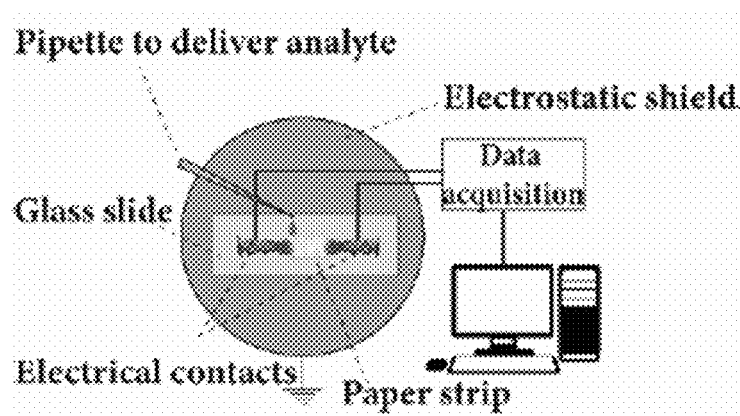

The devices used in the experiment (FIG. 23a-c) consisted of a sample holder with two clips and electrodes mounted on a glass slide. The devices were connected to a data acquisition system (National Instruments-USB 6341 Data Acquisition (DAQ) and a computer with a custom LabVIEW program (FIG. 23b). The open circuit voltage (Voc) of the paper device was measured as a function of time as buffer, aptamer, and Zika were added to the sensor illustrated in FIG. 23a. The glass slide was located inside a grounded copper enclosure to shield and improve the signal-to-noise ratio. Paper strips (0.2-0.3 cm×1 cm) used in the devices were manually cut from a standard printer paper and were contacted with silver paint (from Ted-Pella). These paper devices were then coated with appropriate analytes such as de-ionized (DI) water/buffer/aptamer and buffer/Zika solutions.

Figure 23C:
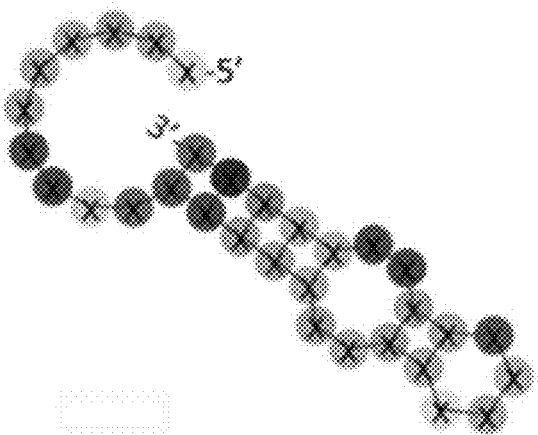

A 1× concentration of Phosphate Buffer Solution (PBS) can be used with 1 milli Molar (mM) Magnesium Chloride as a buffer solution. The Zika aptamers were reconstituted as per BasePair Biotechnologies Inc. by mixing the dried aptamers in resuspension buffer also provided by the manufacturer. The aptamer solution was then diluted to working concentration of 100 µM using an aptamer folding buffer followed by heating to 90° C.-95° C. for 5 minutes. The resulting aptamer solution was then diluted to 1 µM solution using the 130 buffer. 1 µM aptamer had approximately $1.2 \times 10^{12}$ aptamers in 2 µl volume (calculated from the Avogadro number present in 1 M concentration in 1 liter). The aptamer used in our experiments had a thiol end group and consisted of 32 nucleotide-chain that folded to bind with Zika SF9 envelope protein. FIG. 23c shows the schematic of the structure of the aptamer. The Zika was obtained from Zeptometrix and was diluted with 40 µl of TCID_50 Zika stock solution in 160 µl buffer. The number of Zika viruses in 2 µl volume was $\sim 7 \times 10^7$, estimated in the same manner above.

Results and Discussions

Figure 24:
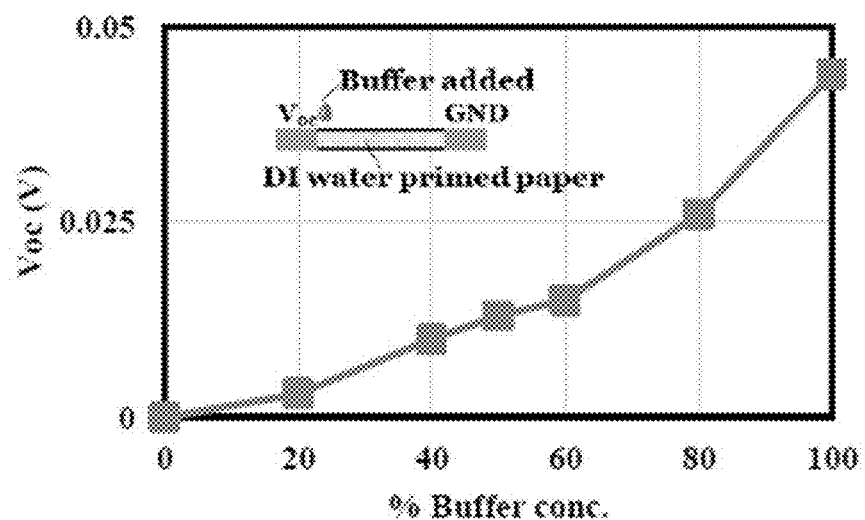

The open circuit voltage (Voc) of the senor containing DI water with the buffer solution introduced on the anode is shown in FIG. 24. The $V_{oc}$ is this case was measured immediately after the buffer was added to the anode region. $V_{oc}$ diminishes as a function of time as the buffer diffuses in the paper and its concentration gradient diminishes.

Figure 25A:
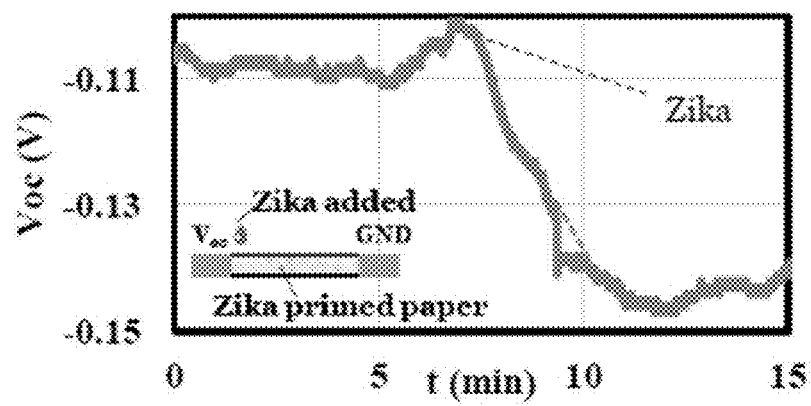
Figure 25B:
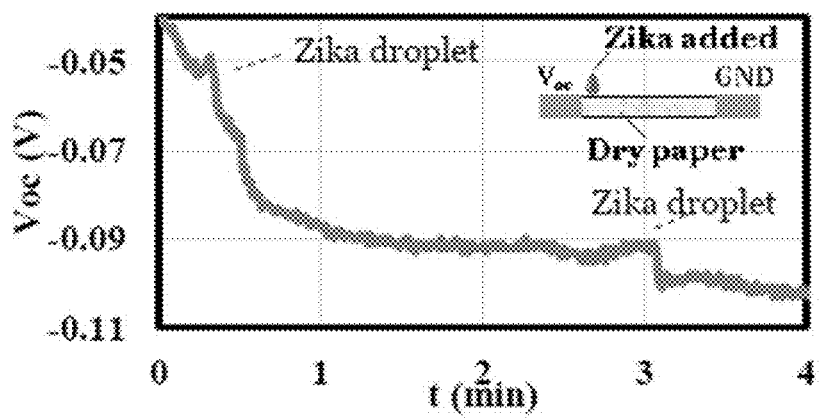

The Zika virus has a small residual negative charge (FIG. 25a) that reduces the Voc as soon as it is added to the sensor. FIG. 25a-b shows the response of the sensor when Zika was added. The initial rise in FIG. 25a is due to the pipette tip approaching the sensor to deliver the Zika. FIG. 25b shows another run with the Zika added in the beginning and later at 3.1 min. In both cases the sensor output reached a steady-state value. This indicates that the concentration gradient introduced by the addition of Zika did not change as a function of time and it appears that the Zika became immobilized in the paper.

In the second case (FIG. 25b), the paper was not primed with aptamer and the change in Voc was due to the residual charge of the Zika and buffer ions that accompany the Zika as part of its solution. It is also possible that the printer paper we are using have its own impurities that in the presence of Zika+buffer became ionized. Zika is spherical with 40 nm diameter and it is expected to get entangled in the paper pores. If Zika was mobile, the resulting Voc would diminish as a function of time as the Zika diffuses and reduces its concentration gradient. In separate experiments with buffer solutions alone not shown here, the sensor response diminished after the initial introduction of the buffer at the anode indicating that the buffer ions could diffuse in the paper diminishing their initial concentration gradients.

Figure 26:
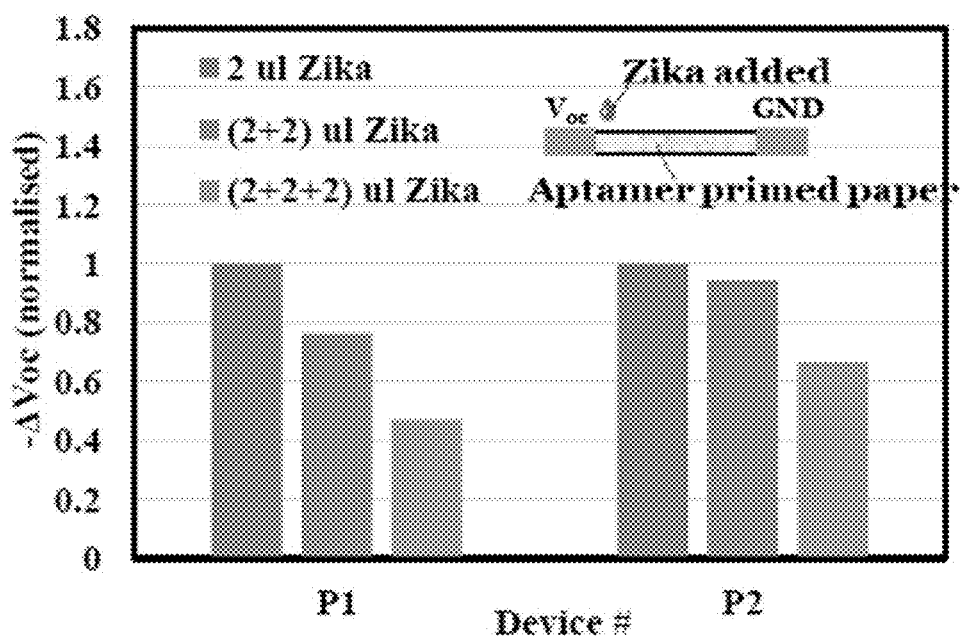

FIG. 26 shows the Voc change $\Delta Voc(t) \sim Voc(t=0) - Voc$ as a function of Zika concentration using a paper device primed with aptamers and buffer. Once all the resident aptamers bind with Zika, the only changes in the device charge content and its gradient are introduced by the additional Zika alone that has negative residual charges. Successive additions of Zika (used to increase its concentration) introduced larger changes in Voc followed by smaller changes once all the resident aptamers were saturated (FIG. 25b) and $\Delta Voc$ became smaller at the end. The average "point" sensitivity in these devices were 0.26 nV/Zika calculated at $\Delta Voc$ of ~18 mV for 2 µl Zika. The sensitivity was nearly the same for 4 µl Zika in device P1 but not in device P2 (FIG. 26). The paper-based sensor's output response had an rms noise voltage of 2 mV and the minimum detectable voltage was 2 mV that resulted in the MDS of $2.4 \times 10^7$ Zika.

Figure 27A:
Figure 27B:
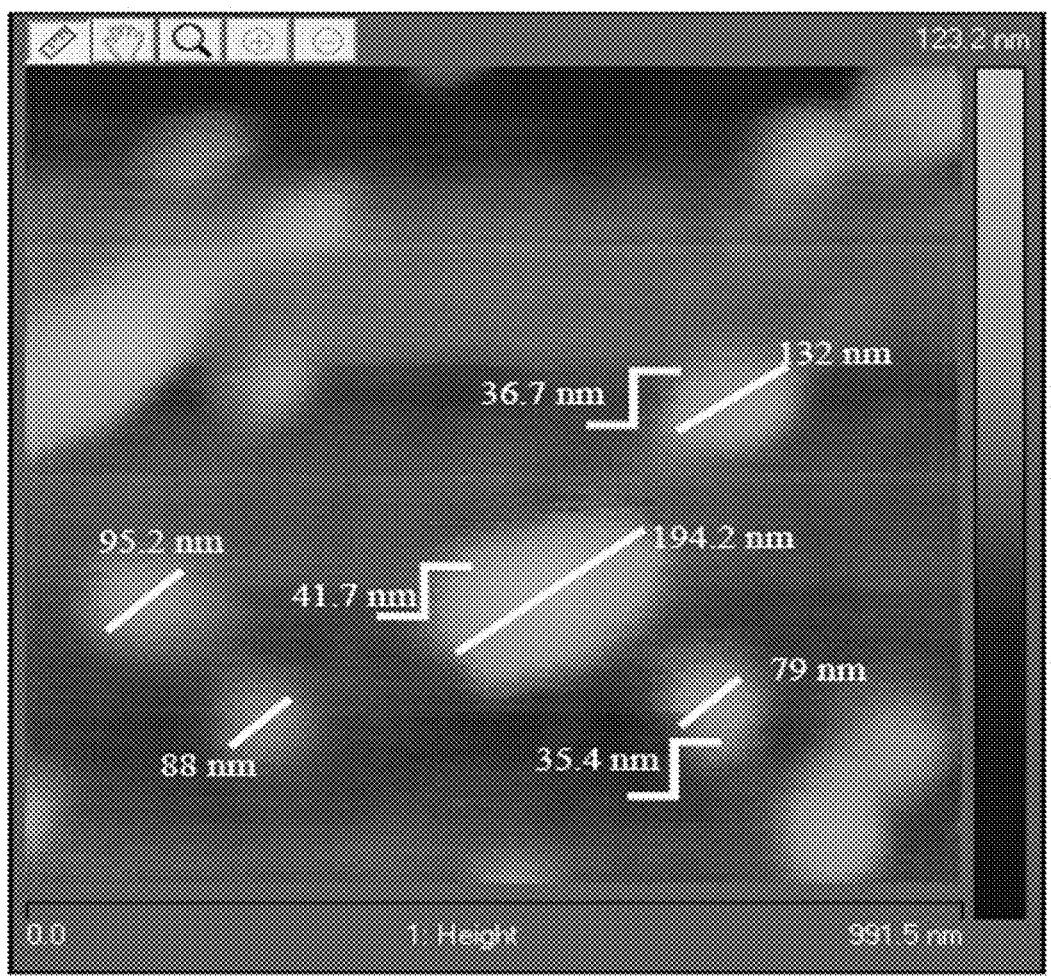

To verify the presence of aptamers and Zika in the paper-based devices, two additional experiments were performed. The first series of experiments used atomic force microscopy (AFM) to image Zika-coated regions of the paper-based device as shown in FIG. 27a. Although one can see large Zika complexes, individual Zika viruses could not be resolved. The paper has very large surface roughness in excess of 2 µm rms that prevented performing high spatial resolution scans. AFM scans were then performed on aptamers and Zika deposited on gold-coated glass samples. As can be seen in FIG. 27b one could resolve individual Zika viruses on gold.

Figure 27C:
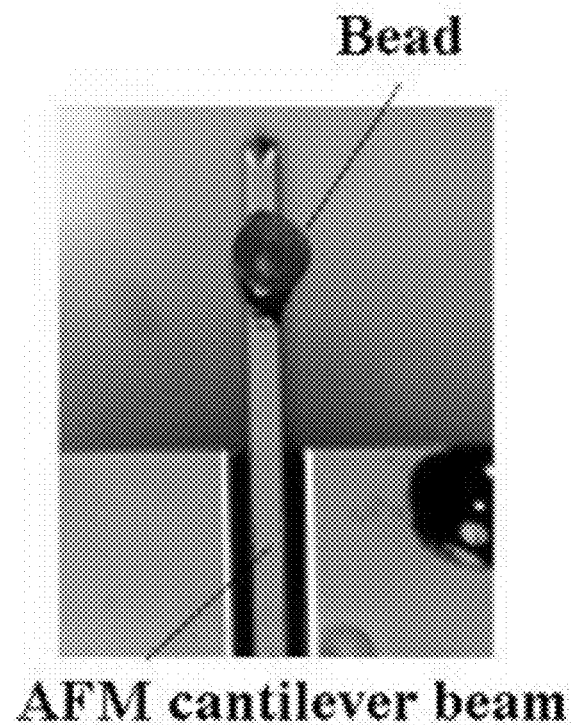
Figure 27D:
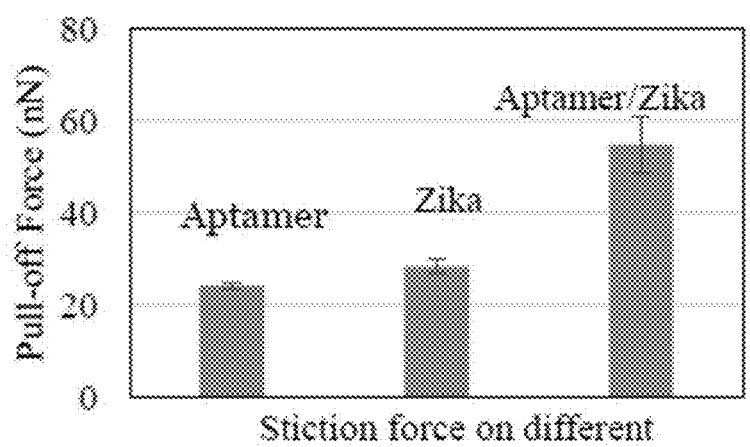

Next, AFM studies using AFM probes with an aptamer-functionalized bead (FIG. 27c) were carried out. These studies showed that the aptamer-functionalized AFM probe (FIG. 27c) measured larger stiction forces with papers coated with aptamers than Zika papers with aptamers or Zika alone as shown in FIG. 27d. The stiction force of Zika/aptamer/paper was higher due to aptamer-specific binding with Zika on the aptamer/paper.

Figure 28:
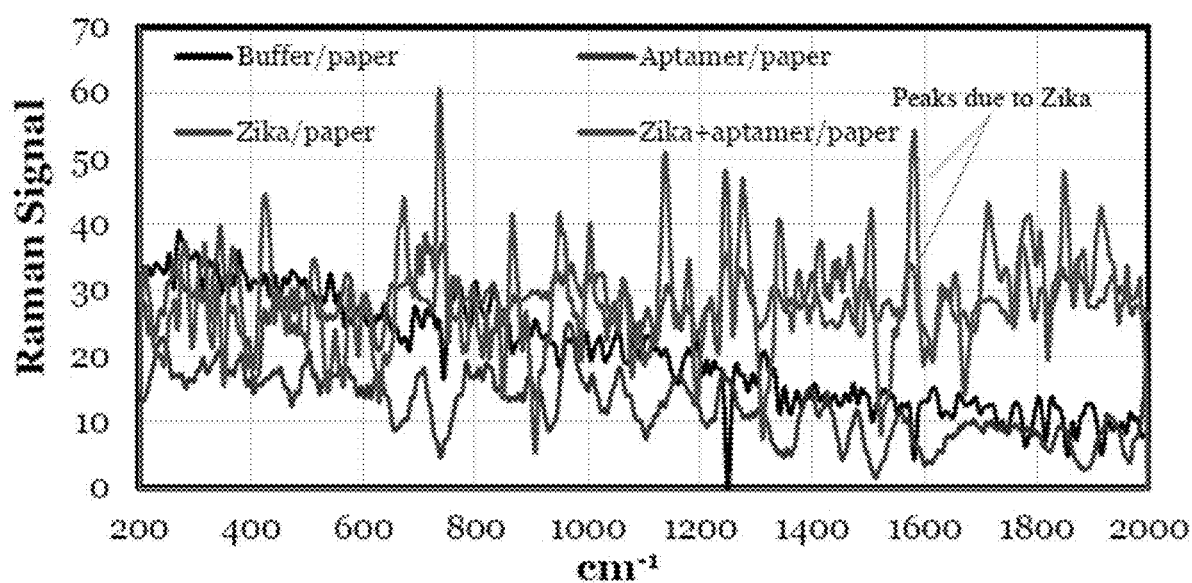

The second set of experiments used Raman spectroscopies on paper-based devices coated with different analytes. The Raman spectra shown in FIG. 28 are from different regions of the paper coated with aptamers, Zika and Zika/aptamers. A DeltaNu spectrometer with Examiner 785 Raman unit was used in these experiments. The amount of aptamers used in priming these samples were 10 µl with 1 µM concentrations and the Zika concentration was $1.7 \times 10^8$/µl and the amount used in each application was 1 µl. The buffer solution was 1 µl of 1×PBS with 1 mM $MgCl_2$. The Raman peak due to Zika was around 1590 $cm^{-1}$.

Figure 29A:
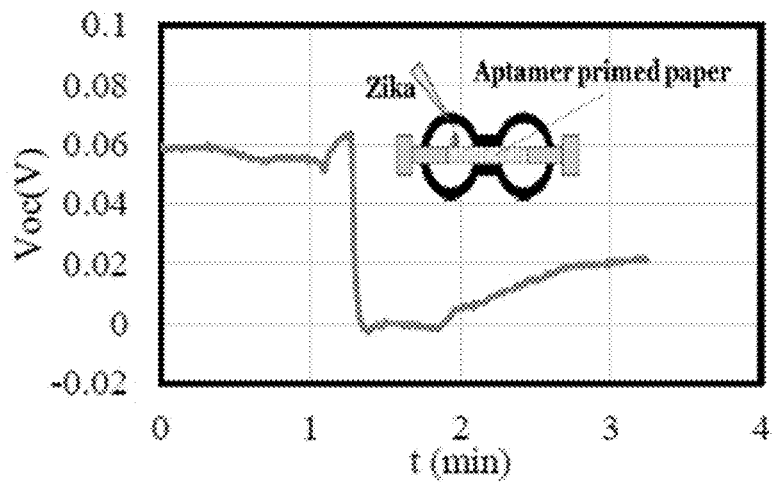
Figure 29B:
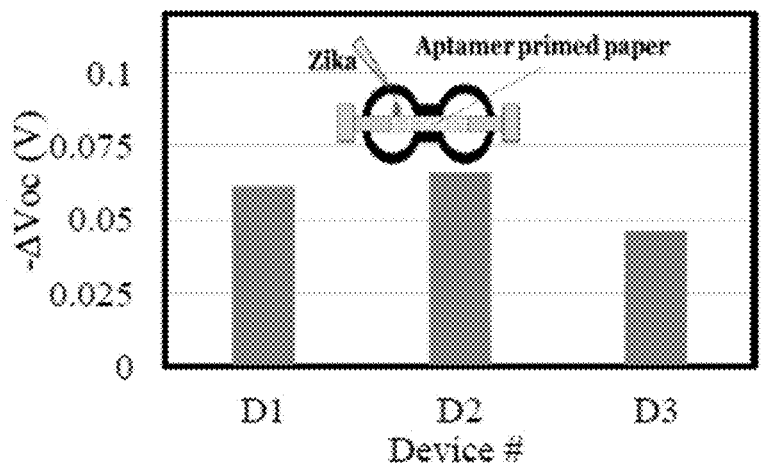
Figure 29C:
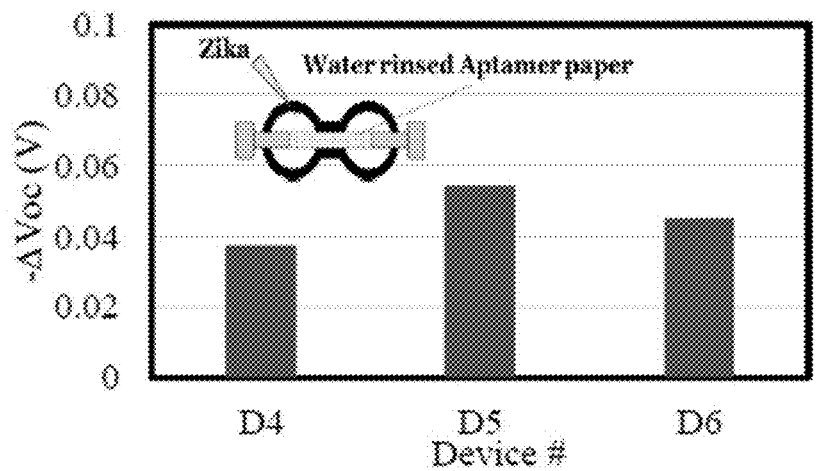
Figure 30A:
Figure 30B:
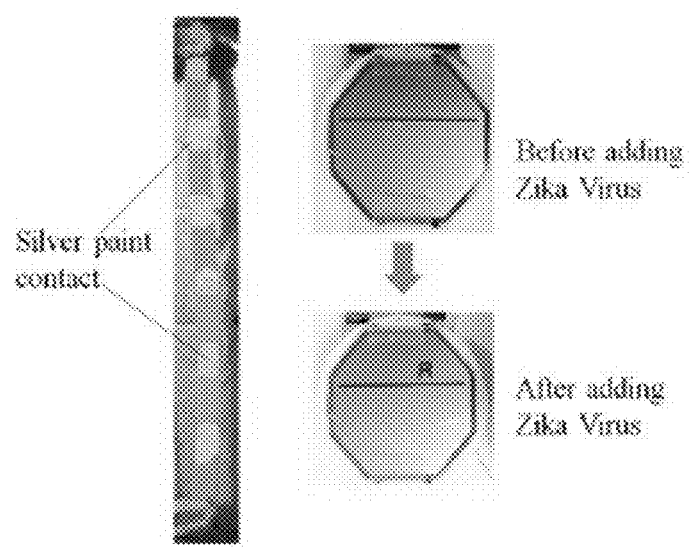

Printed patterns on paper were then used followed by adding silver paint contacts as shown in FIG. 23*a* and FIG. 29*a-c* insets. The purpose of the printed device is to clearly show the location of the Zika solution (or fluids that may contain Zika) on the device. FIG. 29*a* shows the Voc-time response for paper-based devices (D1-D3). The ΔVoc in these devices are shown in FIG. 29*b*. It was verified that the aptamer stayed and was resident in the paper even after rinsing the paper with DI water. FIG. 29*c* shows the response of adding Zika on three different aptamer-primed sensors (D4-D6). The Voc levels in FIG. 29*c* are similar and consistent with that of the aptamer-primed device in FIG. 29*b*.

The actual interactions between different components in the paper matrix is quite complex and the sensor response depends on the history of the paper, temperature, air current on the sensor, and other environmental factors. The results shown here had a standard deviation of ~2 mV from run to run. Uniformity of the electrical contacts can be a concern that can be addressed using 3-D printing. Another very important source of error was in making sure that the paper sensor was not saturated with the analytes introduced at each step. When the paper was saturated, the addition of Zika resulted in a thin layer of liquid above the paper sensor and Zika did not incorporate in the paper resulting in unreliable sensor output. The sensor was also very sensitive to spurious environmental electric fields generated by us and other objects nearby that could be addressed by proper grounding.

Electronic Readout

The possibility of detecting the virus from the paper-based sensor was the explored in a form of direct electronic readout through a liquid crystal diode (LCD) instead of measuring the open circuit voltage using a digital voltmeter. The LCD was configured to display a letter such as "A" once the paper sensor voltage reached a threshold value generated by the presence of sufficient number of Zika viruses. In order to demonstrate the feasibility of such application, we used an LCD screen from a digital watch and experimentally obtained turn-on voltage for a single display segment to be ~100 mV. From the previous results we observed that addition of Zika resulted in Δ Voc~50 mV. Six paper sensors connected in series were used to generate ~300 mV (FIG. 30*a*) that was sufficient to power many readout devices including LCDs. The external LCD load did not draw more than 0.1 mA current to cause internal sensor resistor to become important. As can be seen in FIG. 30*b*, the LCD displayed "A" upon adding Zika. The LCD can be replaced by electronic-ink display which requires much lower voltages/power eliminating the necessity of using many devices in series.

The paper-based sensors we constructed and reported here were very reproducible as long as they were not saturated (with buffer or water) and as long as they were grounded properly. Their "point" sensitivity of 0.26 nV/Zika and their minimum detectable signal (MDS) of $2.4\times10^7$ Zika are quite good given their simple structures and ease of operation. Selectivity of this sensor as well as other aptamer-based sensors are limited by the selectivity of their respective aptamers that can be modified to achieve better selectivity if needed. In the case of paper-based sensors discussed here, the selectivity may also be affected by viruses becoming immobilized in the paper even if they are do not bind with the resident aptamer. These other viruses can be removed by mildly washing them away that will not affect the Zika-aptamer complexes appreciably. The real-world application of Zika paper sensors will involve presence of bodily fluids such as urine or sweat or saliva. These biofluids are very complex and proper filtering on the sensor will be used to remove their components that may affect the paper sensor operation adversely.

As with any sensor development, the research and development efforts have many different stages. It usually starts with developing a transduction mechanism using modified "clean" samples and progresses toward more realistic samples in real world. The present work describes the transduction phenomena of sensing pure Zika virus using a paper-based potentiometric device. The paper-based sensors allow: a) using paper-based sensors to detect the whole virus and b) using resident aptamers in the paper to bind with Zika. The sensor's selectivity comes from its resident aptamer.

The paper can also be used as an active sensing medium located over electrodes connected to the measurement apparatus. In this approach, the paper can be peeled off and replaced with a fresh paper. Paper itself can be used as a filter preventing larger particles from reaching the sensitive layers in intimate contact with the electrodes.

In one example, a paper based biosensor can be formed to detect a selected virus. The paper based biosensor can comprise a paper substrate. The paper substrate can be comprised of a selected type of cellulose based paper. The paper substrate is configured to absorb an analyte to provide a desired level of conductivity. In one example, the analyte can be deionized water. The paper based biosensor can further comprise a first conductive electrode on a first side of the paper substrate and a second conductive electrode on a second side of the paper substrate. The first conductive electrode and the second conductive electrode can be printed on the paper substrate. The second conductive electrode is configured to have a voltage differential with the first conductive electrode. A plurality of aptamers can be functionally attached to the paper substrate between the first conductive electrode and the second conductive electrode, wherein the plurality of aptamers are configured to bind with a selected virus when the selected virus is deposited on the aptamers.

When the selected virus binds with the aptamers, a change in the voltage differential can occur to enable the selected virus to be detected. The change in voltage may be detected with a voltmeter. Alternatively, a liquid crystal display (LCD) sensor or an electronic ink sensor can be applied to the paper substrate. The LCD sensor or electronic ink sensor can display when a predetermined change in voltage occurs between the first conductive electrode and the second conductive electrode due to the selected virus bonding with the plurality of aptamers.

In one example, an aptamer buffer solution containing the plurality of aptamers can be used to apply the aptamers to the paper substrate. The aptamer buffer solution is configured to deposit at a selected location on the paper substrate between the first conductive electrode and the second conductive electrode. A virus buffer solution containing a predetermined concentration of the selected virus can then be applied to the paper substrate. The virus is configured to bond with the aptamers.

Impedance Based Electrical Sensors

In yet another example, a method of detecting a virus can include exposing a sensor surface to a fluid sample containing a suspected virus, where the sensor surface is modified with molecular recognition groups selective for binding to the virus. An impedance spectrum of the sensor surface can be measured, e.g. across interdigitated electrodes. As with other examples, the presence of virus changes the device response, in this case as a measured impedance spectrum, in a unique signature response for a particular virus. The measured impedance spectrum can be compared with an impedance spectrum indicating the presence of the virus bound to the molecular recognition group. The method can also include outputting a detection signal.

In the context of these sensors, impedance spectroscopy can refer to applying an alternating voltage at a series of frequencies to molecular recognition groups that may have viruses bound thereto. The impedance can be measured at each of the frequencies, and the impedance values at the multiple different frequencies can form an impedance spectrum. The impedance spectrum can change depending on whether viruses have bound to the molecular recognition groups or not. Therefore, similar to the other examples described above, the present of a target virus can be detected by compared the measured impedance spectrum with an impedance spectrum that signifies that the target virus is present.

In some examples, the sensor can include an electrode pair separated by a sensor surface. The sensor surface can be modified with molecular recognition groups such as aptamers as described above. The electrodes can be connected to a network analyzer that is capable of applying an alternating voltage over a span of frequencies and measuring the impedance between the electrodes. The network analyzer can be the same type of instrument as described above.

Figure 31:
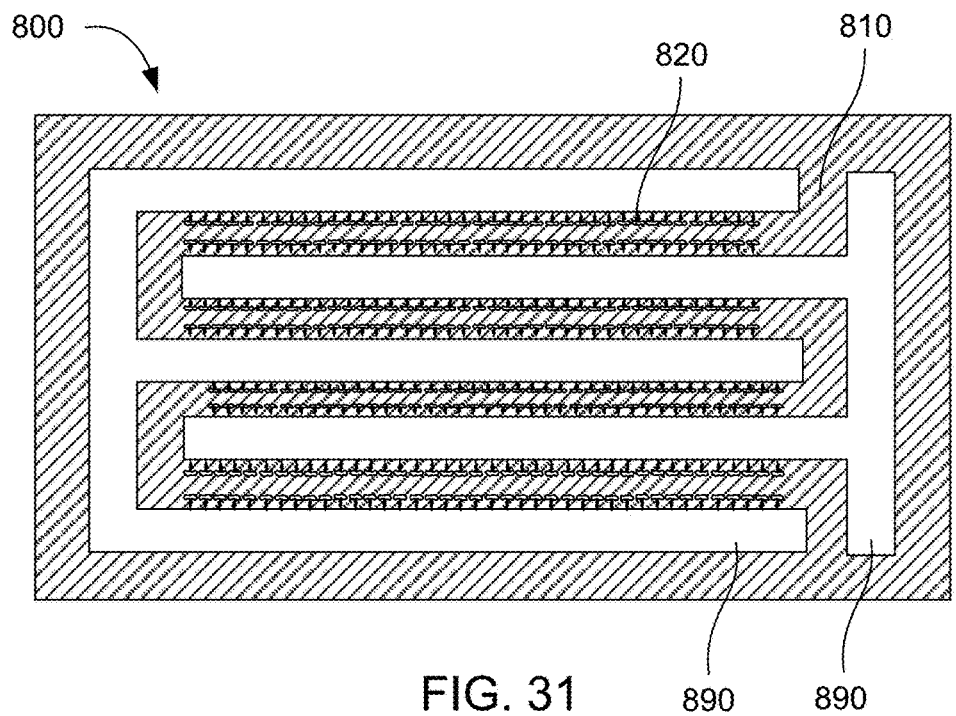

FIG. 31 shows a top-down view of an example sensor 800 that includes two electrodes 890 separated by a sensor surface 810. In this example, the electrodes are shaped as an interdigital transducer. The sensor surface between electrodes can be coated with aptamers 820. In some examples, the electrodes can also be coated with aptamers (e.g. inner walls facing one another across the electrode gap). When viruses bind to the aptamers, the impedance spectrum of the impedance between the electrodes can change. Therefore, the target virus can be detected by comparing a measured impedance spectrum of the electrodes with an impedance spectrum of the sensor when the target virus is known to be bound to the aptamers.

Interdigital transducers provide a large active surface for the viruses to attach and contribute to the structure's capacitance and resistance. These corrugated electrodes work particularly well in providing larger active surface areas. The electrode-electrode distances are set by the aptamer-virus-aptamer length. Typically, electrode gap distances within about 5% of the aptamer-virus-aptamer length can be useful. Platinum and gold are both particularly suited for impedance IDT based sensors. The impedance spectroscopy of IDTs can be used to identify presence of viruses. Usually large changes in the device capacitance (both parallel and series) at lower frequencies are observed. The IDTs resistance (both parallel and series) is also reduced in the presence of viruses. One method to capture these changes is to use square waves in measuring the IDT's response to viruses. The combination of changes that occur in the capacitance and resistances of the IDTs result in a very unique square pulse excitation response of the IDTs. (see FIG. 32).

In certain examples, the impedance spectrum can be made up of measurements of the S21 S-parameter across a range of alternating voltage frequencies. The span of frequencies included in the impedance spectrum can be from about 2 GHz to about 20 GHz in some examples, or from about 8 GHz to about 18 GHz in some examples.

Figure 32:
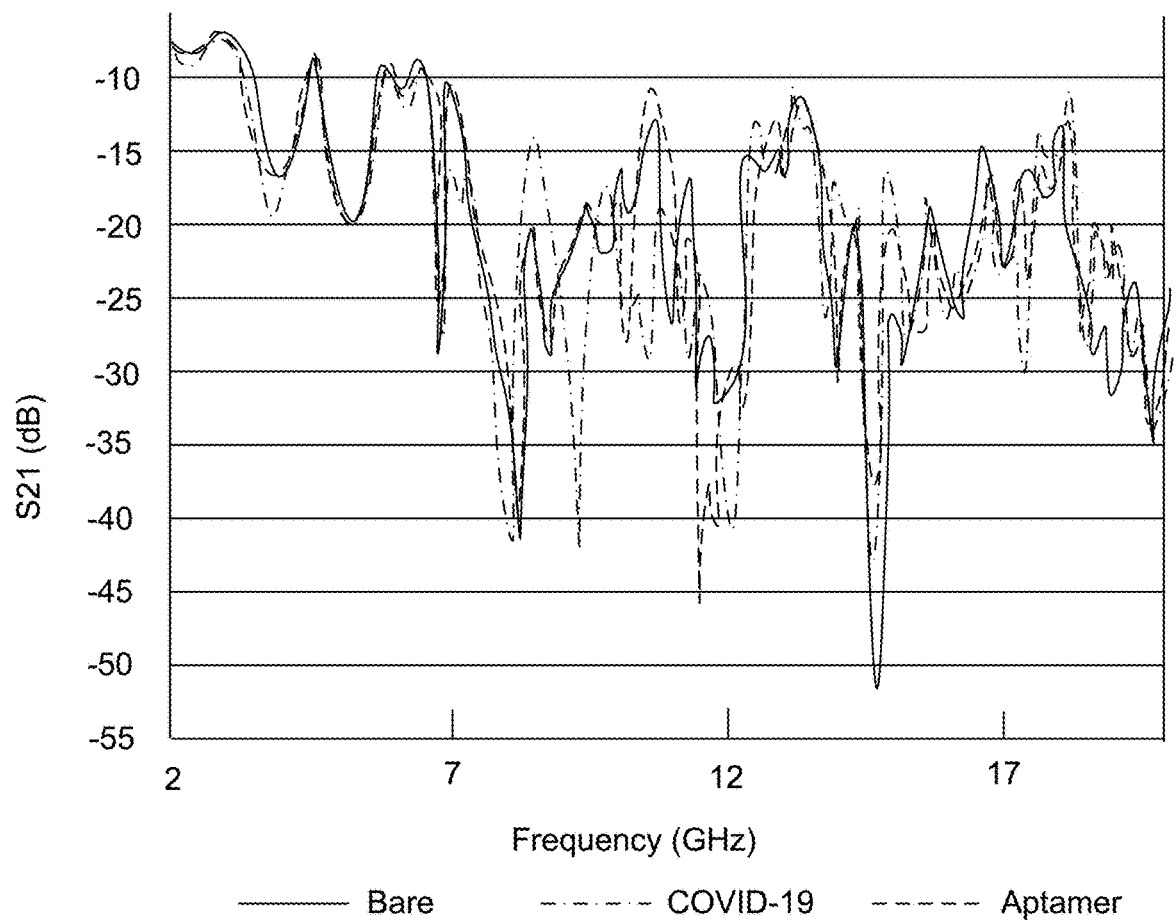

As a specific example of an impedance based sensor, a network analyzer was used to measure impedance spectra of a surface before and after the addition of aptamers and SARS-CoV-2 virus (i.e., COVID-19). The impedance spectra of the bare surface, of the surface with aptamers attached, and of the surface with aptamers and viruses, are shown in FIG. 32.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A vertical nano gap tunneling current biosensor, comprising:
 a semiconductor substrate;
 a first electrode oriented on the semiconductor substrate and configured to be connected to a parameter analyzer, the first electrode having a conductive sample surface including molecular recognition groups attached to the surface which are configured to bind with a selected virus, and having an open region located above the first electrode such that the a sample can be introduced onto the surface from outside of the biosensor;
 a second electrode spaced from the first electrode with a portion of the electrode protruding into the open region to form a nano-gap between the first electrode and the second electrode, the nano-gap having a tunneling gap distance to enable a tunneling current between the first electrode and the second electrode when a voltage differential is provided between the first electrode and the second electrode; and
 a dielectric layer separating the first electrode and the second electrode,
 wherein the parameter analyzer is configured to detect a change in the tunneling current through the nano-gap over a range in voltage and the change in the tunneling current is used to identify when the selected virus is bound to the molecular recognition groups.

2. The vertical nano gap tunneling current biosensor of claim 1, wherein the semiconductor substrate comprises silicon and a passivation layer is oriented between the semiconductor substrate and the first electrode.

3. The vertical nano-gap tunneling current biosensor of claim 1, wherein the molecular recognition groups include at least one of aptamers, antibodies, and antigens.

4. The vertical nano-gap tunneling current biosensor of claim 1, wherein the selected virus is either SARS-CoV-2 or ZIKA.

5. The vertical nano-gap tunneling current biosensor of claim 1, wherein the first and second electrodes are formed of gold.

6. The vertical nano-gap tunneling current biosensor of claim 1, wherein the dielectric layer is silicon dioxide.

7. The vertical nano-gap tunneling current biosensor of claim 1, further including a hydrophobic layer coated on a top surface of the second electrode.

8. The vertical nano-gap tunneling current biosensor of claim 1, wherein the tunneling gap distance is formed to have a selected gap size based on the selected virus and the tunnel gap distance is orthogonal to a plane of the conductive sample surface.

* * * * *